US011531076B2

(12) United States Patent
Ajoy et al.

(10) Patent No.: US 11,531,076 B2
(45) Date of Patent: Dec. 20, 2022

(54) WIDE DYNAMIC RANGE MAGNETIC FIELD CYCLER AND ULTRA PORTABLE OPTICAL NANODIAMOND HYPERPOLARIZER

(71) Applicant: THE REGENTS OF THE UNIVERSITY OF CALIFORNIA, Oakland, CA (US)

(72) Inventors: Ashok Ajoy, Fremont, CA (US); Emanuel Druga, Castro Valley, CA (US); Alexis Morabe, Temecula, CA (US); Kristina Song Liu, Berkeley, CA (US); Alexander Pines, Berkeley, CA (US); Raffi Nazaryan, Tujunga, CA (US)

(73) Assignee: The Regents of the University of California, Oakland, CA (US)

( * ) Notice: Subject to any disclaimer, the term of this patent is extended or adjusted under 35 U.S.C. 154(b) by 182 days.

(21) Appl. No.: 16/761,462

(22) PCT Filed: Nov. 1, 2018

(86) PCT No.: PCT/US2018/058755
§ 371 (c)(1),
(2) Date: May 4, 2020

(87) PCT Pub. No.: WO2019/089961
PCT Pub. Date: May 9, 2019

(65) Prior Publication Data
US 2021/0364583 A1  Nov. 25, 2021

Related U.S. Application Data

(60) Provisional application No. 62/641,532, filed on Mar. 12, 2018, provisional application No. 62/581,377, filed on Nov. 3, 2017.

(51) Int. Cl.
*G01R 33/28* (2006.01)
*G01R 33/30* (2006.01)
*G01R 33/34* (2006.01)

(52) U.S. Cl.
CPC ......... *G01R 33/282* (2013.01); *G01R 33/307* (2013.01); *G01R 33/34023* (2013.01)

(58) Field of Classification Search
CPC ............... G01R 33/282; G01R 33/307; G01R 33/34023
See application file for complete search history.

(56) References Cited

U.S. PATENT DOCUMENTS 7,521,928 B2  4/2009  Romalis et al.
8,807,322 B2  8/2014  Cassoni
(Continued)

FOREIGN PATENT DOCUMENTS

EP  2727709 A1  5/2014
WO  2007082048 A2  7/2007

OTHER PUBLICATIONS

International Search Report and Written Opinion, PCT/US2018/58755, dated Apr. 1, 2019, 11 pages.

*Primary Examiner* — Jermele M Hollington
*Assistant Examiner* — Taqi R Nasir
(74) *Attorney, Agent, or Firm* — Miller Nash LLP

(57) ABSTRACT

A system can include: a superconducting or permanent magnet; a high field portion corresponding to the superconducting or permanent magnet, wherein the high field has a range of 0.1-20 T; a low field portion positioned outside of the superconducting or permanent magnet, wherein the low field has a range of 0.01 nT-100 mT; a shuttling mechanism configured to deliver a sample between the low field portion and the high field portion; and a polarization sub-assembly configured to hyperpolarize the sample while the sample is within the low field portion. A device can be configured to (Continued)

cause nuclear spin hyperpolarization in diamond particles such that the hyperpolarization is transferable to at least one of an external liquid or an external solid. A process of hyperpolarizing substances can include applying optical illumination to the substance, irradiating the substance with a series of microwave signals as one of either a single signal or as a frequency comb to hyperpolarize the nuclei in the substance, and relaying polarization to nuclear spins of one of a surrounding solid or fluid.

22 Claims, 36 Drawing Sheets

(56) References Cited

U.S. PATENT DOCUMENTS

| | | | |
|---|---|---|---|
| 2008/0106261 A1* | 5/2008 | Romalis | G01R 33/441 324/304 |
| 2009/0252686 A1* | 10/2009 | Marcus | A61P 43/00 424/9.3 |
| 2013/0327615 A1* | 12/2013 | Cassoni | B65G 21/14 198/617 |
| 2014/0223923 A1* | 8/2014 | Kalechofsky | G01R 33/5601 62/3.1 |
| 2015/0115691 A1* | 4/2015 | Brinager | E21F 13/02 198/300 |
| 2016/0169998 A1* | 6/2016 | Warren | G01R 33/282 204/557 |
| 2018/0149717 A1* | 5/2018 | Jelezko | G01R 33/282 |
| 2019/0369175 A1* | 12/2019 | Schwartz | G01R 33/282 |

* cited by examiner

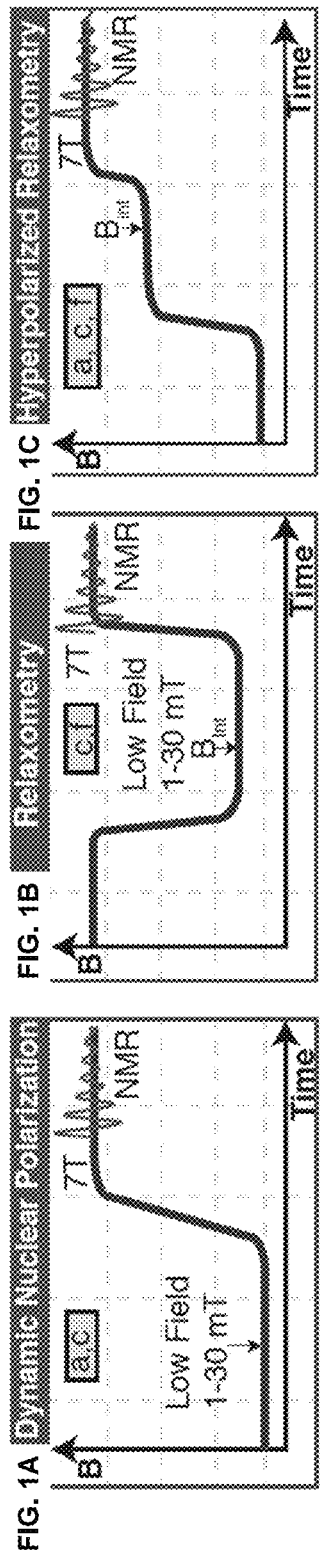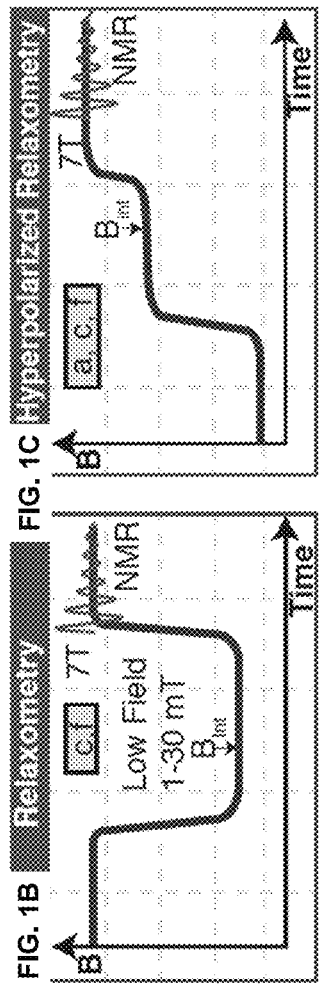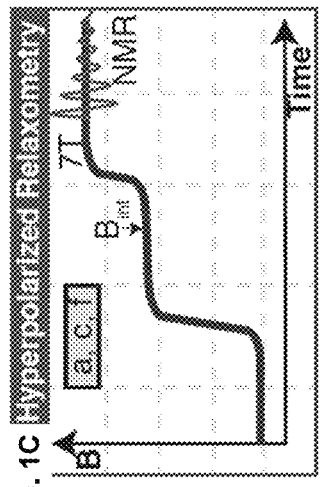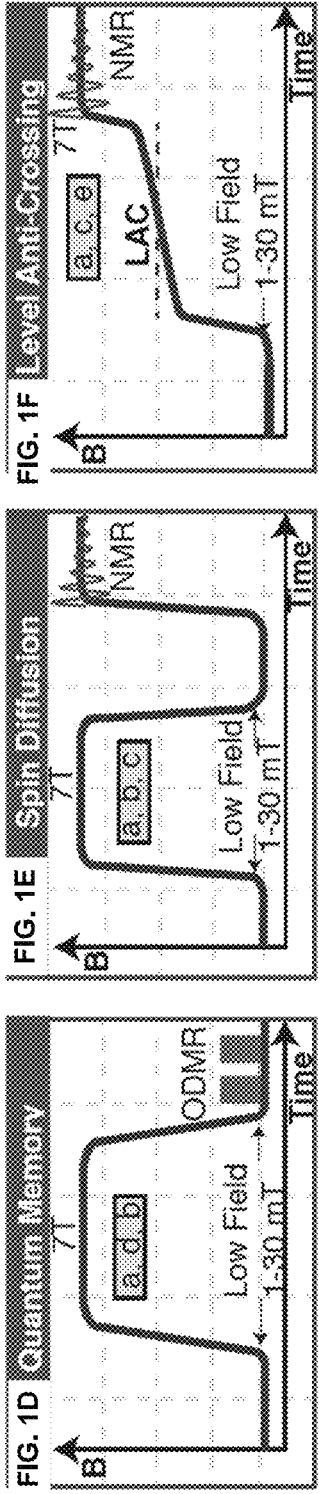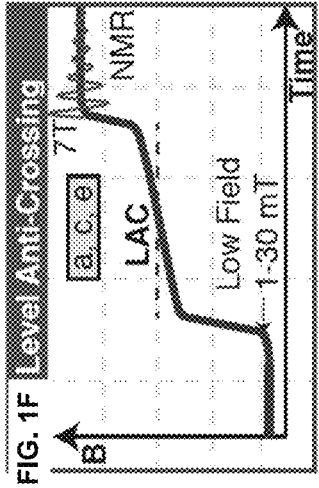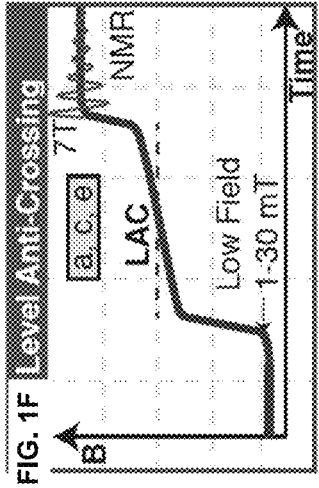

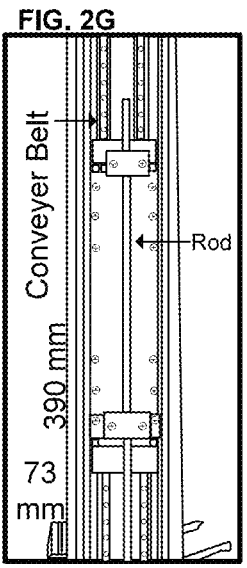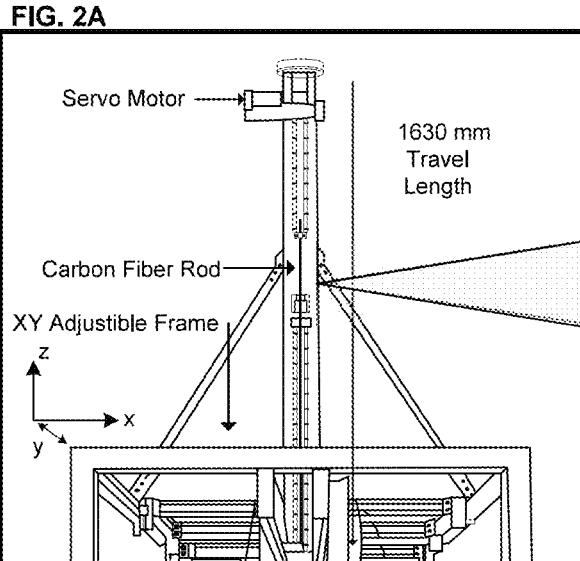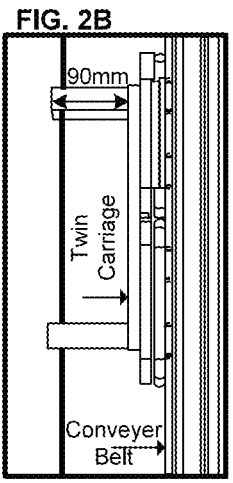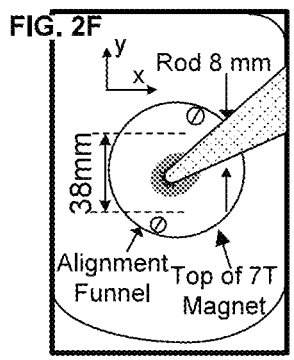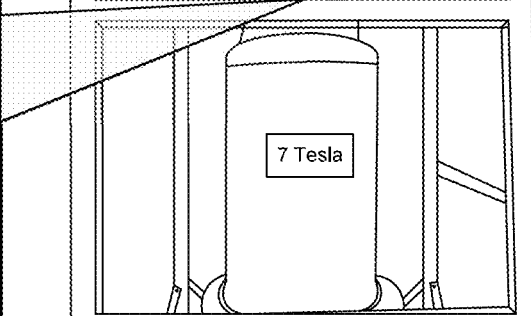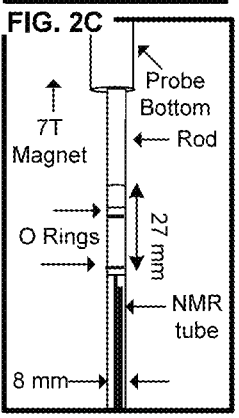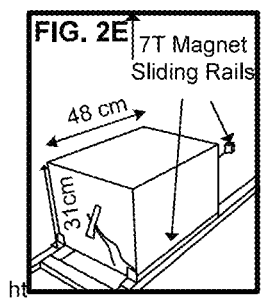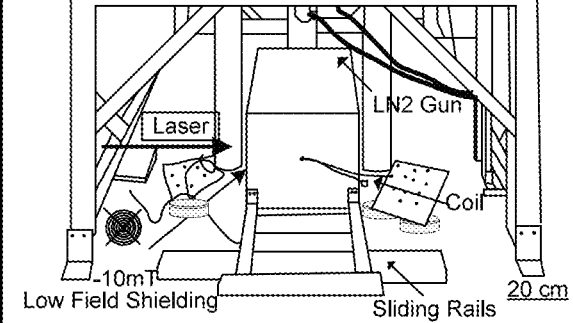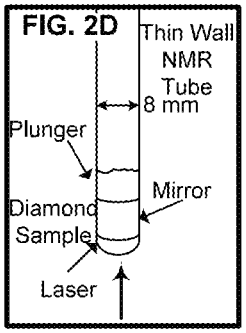

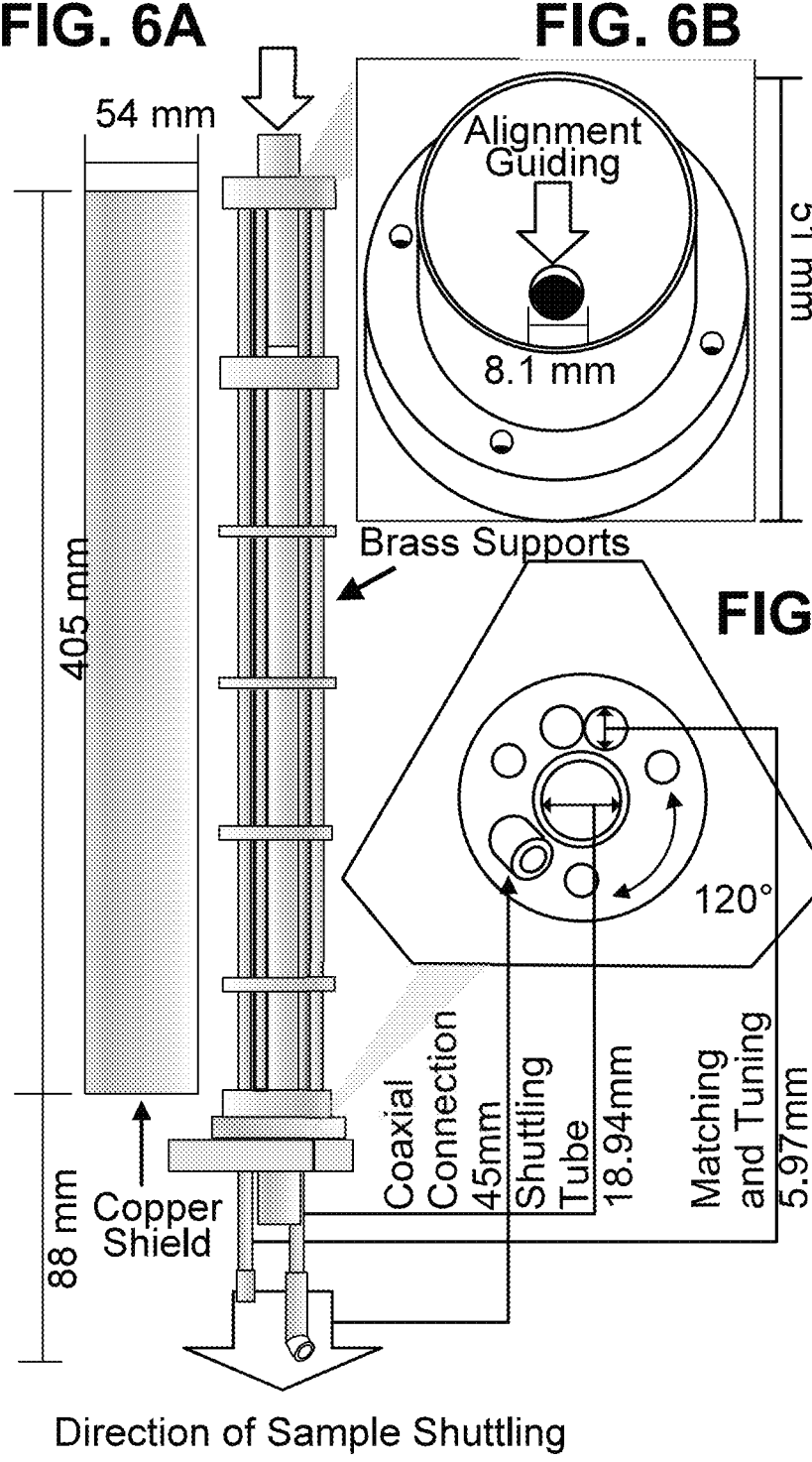
FIG. 6A FIG. 6B FIG. 6C

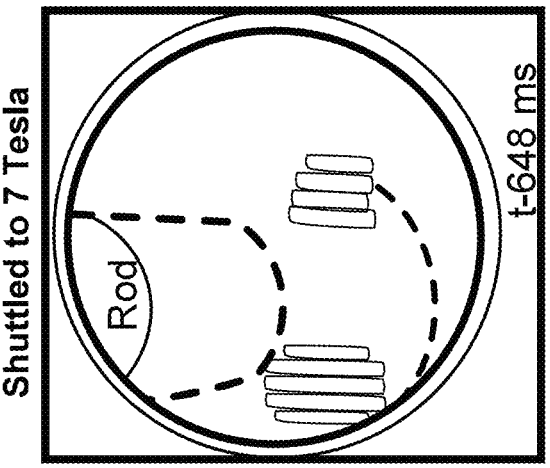
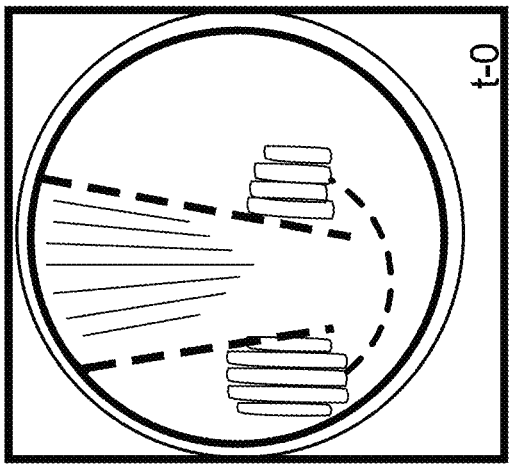
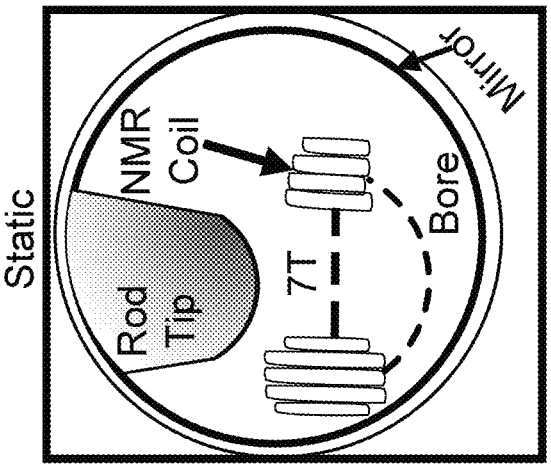

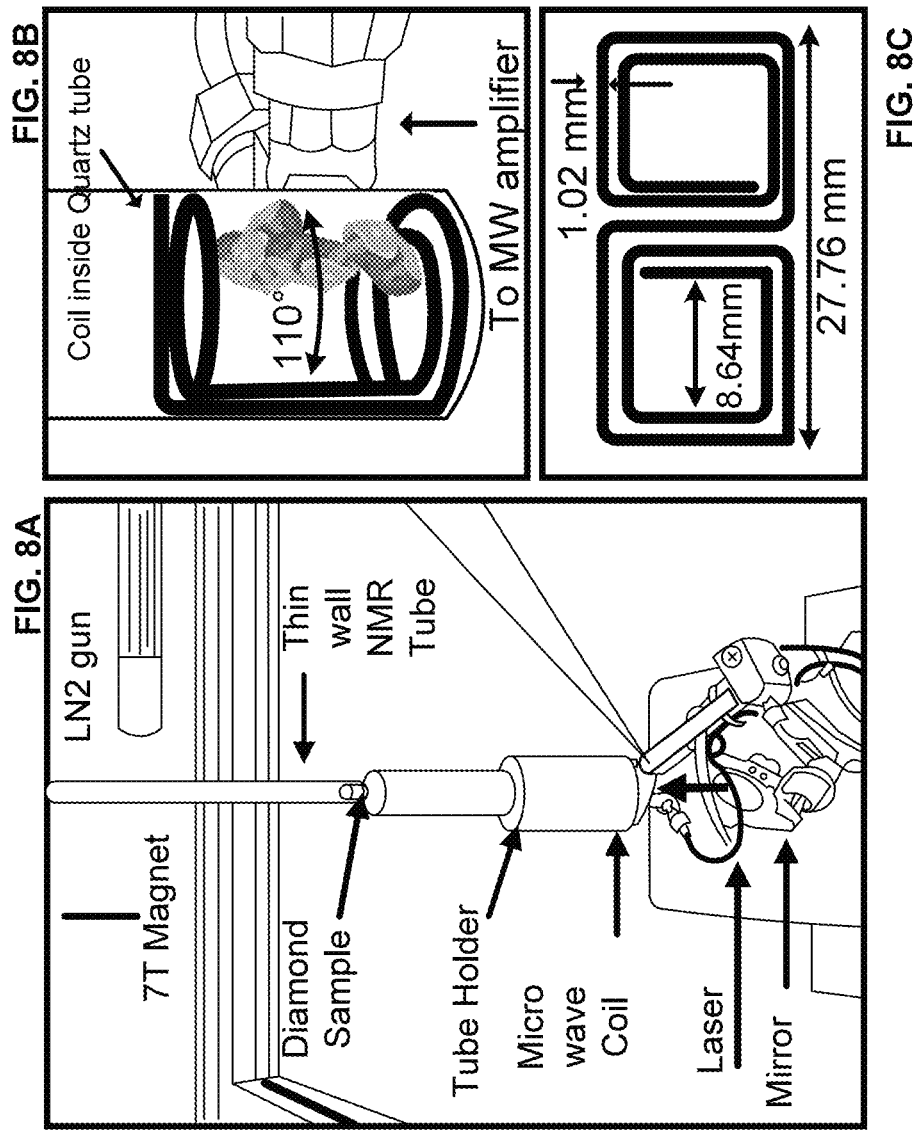

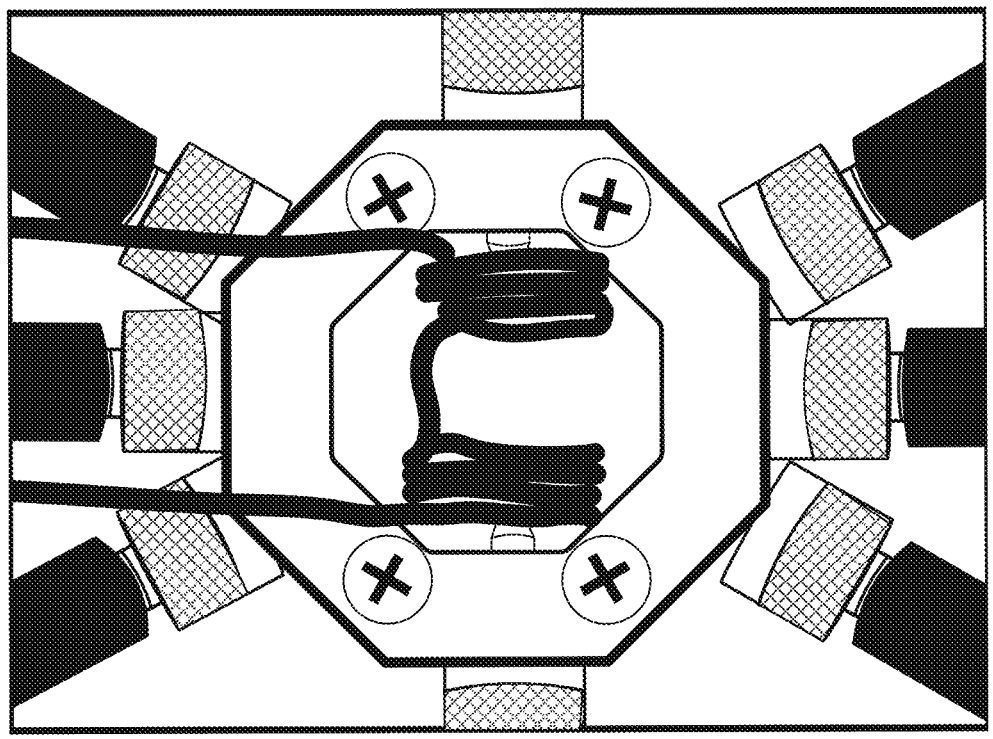
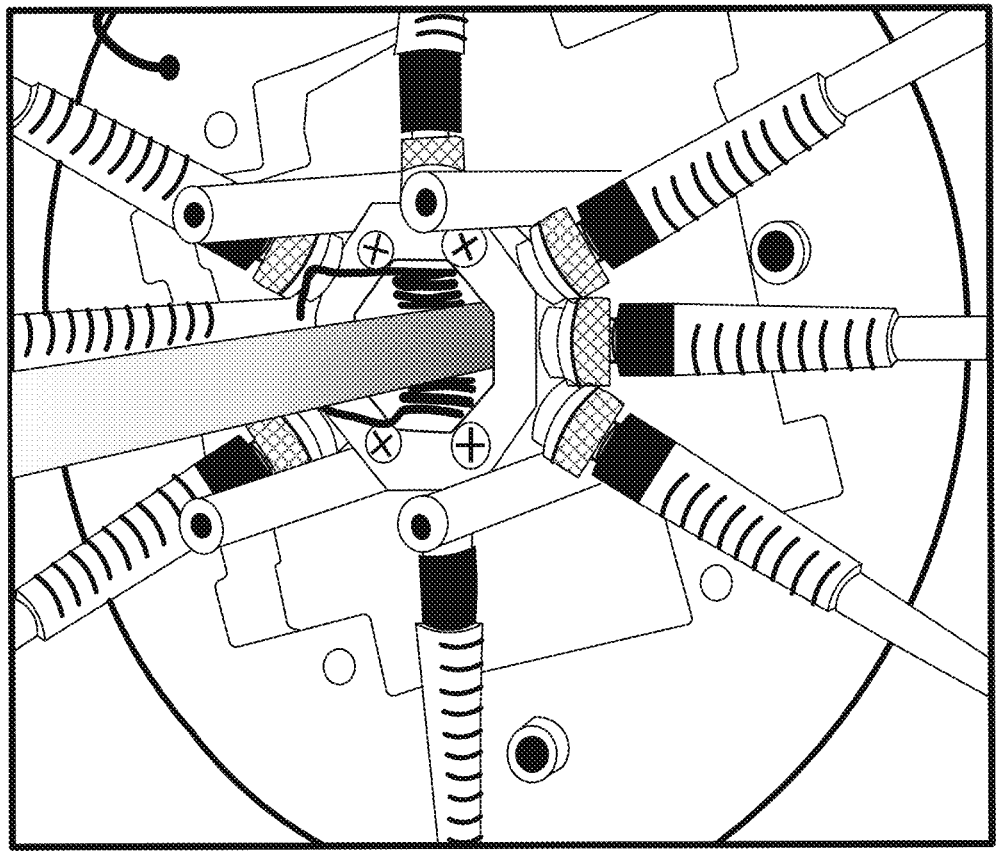
FIG. 42

WIDE DYNAMIC RANGE MAGNETIC FIELD CYCLER AND ULTRA PORTABLE OPTICAL NANODIAMOND HYPERPOLARIZER

CROSS REFERENCE TO RELATED APPLICATIONS

This application is a 371 of International Application No. PCT/US2018/058755 filed Nov. 1, 2018, which claims priority to and the benefit of U.S. Provisional Patent Application No. 62/581,377 filed Nov. 3, 2017, the contents of which are incorporated herein by reference in their entirety. This application also claims priority to and the benefit of U.S. Provisional Application No. 62/641,532 filed Mar. 12, 2018, the content of which is incorporated herein by reference in its entirety.

BACKGROUND

The last few decades have witnessed rapid strides in high-field superconducting magnet technology, with fields >20 T and inhomogeneities better than 1 ppm routinely available, fueling several recent advances in biomolecular nuclear magnetic resonance (NMR). In parallel, there has been a silent revolution in the development of magnetic shielding technology, with specialized alloys of mu-metal providing shielding factors >1 million, and extinguishing fields to <0.1 nT in a relatively large volume.

From a physical point of view, both these extreme regimes of ultra-high and ultra-low magnetic fields provide uniquely complimentary advantages. In quantum information science, for instance, high fields provide a means to store and protect quantum information due to long spin relaxation times ($T_1$). For instance, the electronic spin associated with the nitrogen-vacancy (NV) center in diamond—which has emerged as a promising platform for quantum information processing, simulation and metrology—has a $T_1$ of over 10 ms. In addition, high fields provide the ability to apply highly selective quantum control often with <1 ppm resolution; and gains in measurement, especially bulk inductive spin readout, where SNR scale favorably, $\propto B^{7/4}$. Ultra-low to zero fields, on the other hand, provide the alternative advantages of spin indistinguishably —spins even of completely different species act identically, allowing easy construction of Hamiltonian models in naturally occurring spin networks, and the access to heteronuclear spin singlets with long lifetimes. Moreover, with the absence of any field $B_0$ that acts to truncate the inter-spin couplings, the interaction Hamiltonians are completely isotropic, with an absence of any orientational dependence. This can allow the relatively easy production of nearest-neighbor Heisenberg models in large spin networks in liquids. In dipolar coupled solids, on the other hand, this also leads to fast entanglement generation since there are no disallowed transitions from energy costs set by $B_0$. Finally, it also opens the possibility of ultra-fast quantum control, since there are no speed limits set by the rotating wave approximation.

Nuclear Magnetic Resonance (NMR) and its imaging counterpart (MRI) is a mature, versatile technology widely employed across numerous fields and applications, but suffers from inherently low sensitivity. This has obviated the need for sophisticated and expensive magnets for polarization and signal detection. Dynamic Nuclear Polarization (DNP)—a suite of techniques that serve to enhance the NMR signal—have had far reaching impact in accelerated spectroscopy and imaging since their first successful demonstration two decades ago. Typically, DNP relies on doping the sample with electrons, whose large polarization at high fields and low (cryogenic) temperatures is transferred to the nuclei of interest, hyperpolarizing them, and consequently boosting their NMR signature by orders of magnitude. Indeed, the introduction of commercial DNP systems, including in dissolution DNP, has made signal enhanced NMR more accessible; although at a steep cost (>$1M) of setup and maintenance. Moreover, short nuclear lifetimes usually necessitate hyperpolarization generation at the source, requiring the need to "DNP-retrofit" existing NMR systems at substantial cost overheads.

There is hence a strong desire for inexpensive portable room temperature platforms of DNP generation that can easily be integrated with existing NMR/MRI infrastructure. Chemical DNP methods exploiting the singlet order in parahydrogen have become increasing popular, but still require the use of cyrogens to produce the parahydrogen. Technology based on optically hyperpolarizable nanodiamonds has been proposed as a compelling alternative, exploiting unique spin properties of electronic Nitrogen Vacancy (NV) defect centers that allow them to be optically polarized at room temperature. The long spin coherence times ($T2>100\_s$) of the NV electrons allow this polarization to be coherently transferred to surrounding nuclei. Indeed, these features were exploited recently to develop the first mechanism of optical DNP in diamond particles, hyperpolarizing $^{13}C$ nuclear spins in microdiamonds, and opening the door to the optical hyperpolarization of liquids brought in contact with these high surface area particles.

BRIEF DESCRIPTION OF THE DRAWINGS

FIGS. 1A-1F illustrate an example of polarization transfer and measurement control sequence for DNP excitation and measurement via sample shuttling to 7 T.

FIGS. 2A-2G illustrate an example of a system in accordance with certain implementations of the disclosed technology.

FIGS. 6A-6C illustrate an example of a NMR probe for high speed shuttling which enables high speed shuttling from high to low fields in accordance with certain implementations of the disclosed technology.

FIGS. 7A-7C illustrate exemplary snapshots of high-speed sample shuttling obtained with a camera mounted inside the NMR probe of FIGS. 6A-6C in the 7 T superconducting magnet bore.

FIGS. 8A-8C illustrate an example of a low field DNP setup in accordance with certain implementations of the disclosed technology.

FIG. 42 illustrates a setup detailing a multiple fiber coupled laser configuration.

DETAILED DESCRIPTION

Figures 3A, 3B:
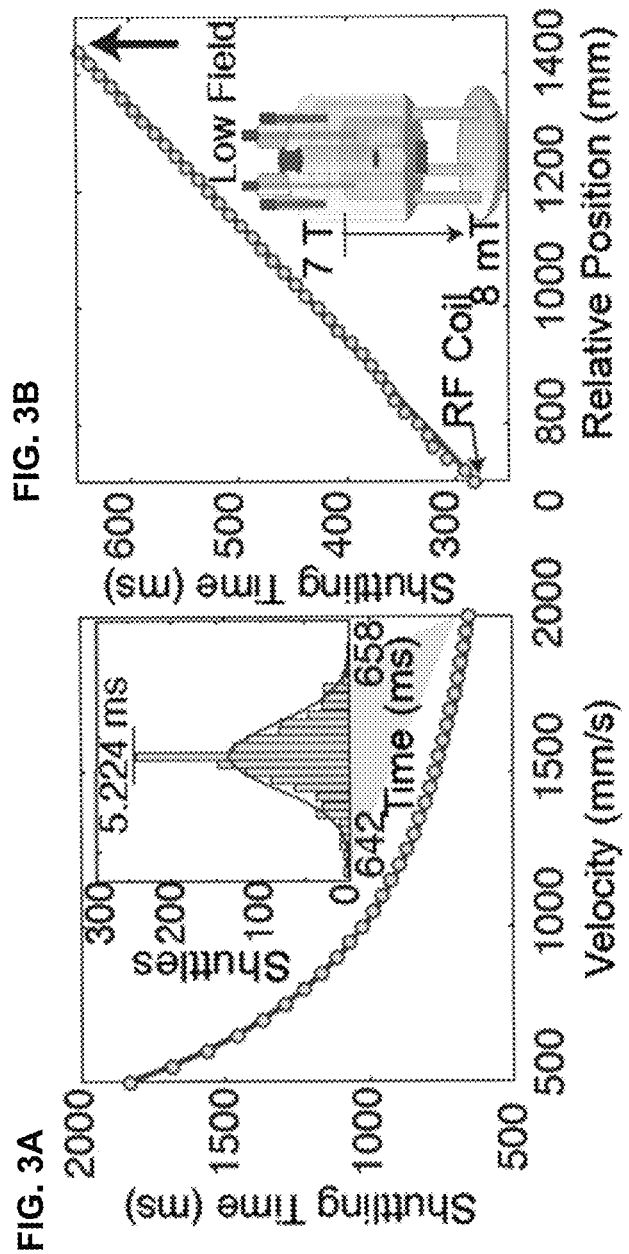
FIGS. 3A-3B illustrate an example of field cycling repeatability and control.

Certain embodiments of the disclosed technology are generally directed to a fast field cycling device capable of sweeping of approximately 10 orders of magnitude of magnetic field from 1 nT-7 T in under 700 ms. This presents a versatile platform to combine the rich power of coherent quantum control and storage at low and high magnetic fields. In particular, the low field advantages of low anisotropy, fast spin manipulation and rapid entanglement growth; and high field gains in spin lifetimes, spin specific control and efficient inductive measurement. The device consists of high-speed sample shuttling between a superconducting magnet and a magnetic shield, with the capability to access arbitrary fields in between with high precision. While generally applicable in a host of problems in quantum information and condensed matter, we employ the device along with a novel technique of dynamic nuclear polarization to determine the spin lifetimes of quantum memories consisting of $^{13}C$ spins in diamond.

Certain embodiments of the disclosed technology are generally directed to a device that is capable of sweeping magnetic fields over a ten order-of-magnitude dynamic range from 1 nT-7 T in under 700 ms. The device works by physically transporting (shuttling) a sample precisely and at high speed between low (1 nT-10 mT) and high field (7 T) centers placed 830 mm apart, exploiting high mechanical precision (50 μm) to achieve arbitrary tunable fields in the fringing field between the two centers. The sample shuttling takes place faster than the $T_1$ times of nuclear spins in a variety of physical systems, which coupled with high resolution inductive detection at 7 T make the system ideally suited to studying nuclear spins at different fields. The system also provides the ability for spin manipulation at the low and high field centers.

There are various versatile applications of the disclosed device. Coupled to the optically addressable NV center qubit, $^{13}C$ spins have garnered attention as forming viable nodes of a quantum information processor due to their long lifetimes, and the fact that they can be rapidly and directly manipulated by the NV center. Their utility as memories have enabled wide gains in quantum sensing, both with respect to sensing resolution and sensitivity—and especially compelling for nanoscale MRI experiments at high fields. However, while their attractive properties stem from their long spin $T_1$ lifetimes, there have been a lack of experiments studying the factors affecting them. Certain embodiments of the disclosed technology are directed to using a novel low field dynamic nuclear polarization (DNP) technique to enhance the bulk $^{13}C$ polarization by about five orders of magnitude at 8 mT and employing the unique field-cycling ability of the instrument, measure the first field-dependent $T_1$ relaxometry of $^{13}C$ spins in diamond over three orders of magnetic field.

The lifetimes of $^{13}C$ spins can be determined by an unambiguous inductive measurement of the bulk nuclear magnetization. In contrast to other, more indirect measurements through closeby NV centers via population swapping and optical readout, this allows one to probe even extremely weakly coupled nuclei, and perform measurements at high fields (7 T) where electronic spin control is otherwise challenging. In order to boost the $^{13}C$ bulk polarization, a novel optical dynamic nuclear polarization technique can be used to enhance it to >800 T level at a field of 8 mT, a gain of about five orders of magnitude. This allows strong, single-shot measurements of $^{13}C$ magnetization by inductive readout at 7 T. Remarkably since low-field for the polarization transfer is exploited, the technique is orientation independent—e.g., does not require any alignment of the sample with respect to the field—and can therefore be employed on powdered diamond and nanodiamonds.

FIG. 1 illustrates an example of a protocol for polarization transfer and measurement. The protocol begins at a low field ($B_{pol}$=1 mT-10 mT), and continuous laser irradiation is applied to optically polarize the NV centers in the diamond, which is then coherently transferred to the $^{13}$C nuclei by means of chirped microwave sweeps across the NV center resonance. In the case of powdered diamond samples, the sweep occurs approximately between $\Delta\pm\gamma eB_{pol}$, where $\Delta=2.87$ GHz is the NV center zero field splitting, and $B_{pol}$ is the polarizing field. Cascading the frequency sweeps lead to enhanced DNP efficiency, and very large polarizations on the $^{13}$C spins can be achieved, e.g., measured to be over 0.1% (enhanced over the thermal polarization at $B_{pol}$ by over 105). The sample is then shuttled rapidly to an intermediate field B, allowed to wait for time t, and then taken to 7 T for measurement, from which the spin life-time $T_1(B)$ can be determined.

In certain embodiments, the field cycler consists of a shuttling tower constructed over a high field (7 T) superconducting magnet with a low field magnetic shield positioned below it (see FIG. 2). A fast conveyor belt actuator stage (e.g., Parker HMRB08) carries the sample in the fringing field of the magnet and into the shield, allowing in effect a 1 nT-7 T field sweep. The sample is carried by a carbon-fiber shuttling rod (e.g., Rock-west composites) that is fastened rigidly on a twin-carriage mount on the actuator stage (see FIGS. 2A, 2B and 2G). Carbon fiber may be selected because of its exceptional strength, low mass and for being immune to eddy-current forces, while the twin-carriage minimizes yaw and aids in alignment, which can be crucial for high sample fill factors.

FIG. 3 highlights the versatile control available in the system—e.g., the ability to tune the shuttler velocity and acceleration (see FIG. 3A) and spatial position for start and stop of motion (see FIG. 3B), and motion trajectories. Shuttling is possible up to a speed of 2 m/s and acceleration of 30 m/s2 over a 1600 mm travel range, with a high positional precision of 50 μm. This control could be exploited in systems with specific level anti-crossings (LACs), for instance in SABRE based DNP with parahydrogen, where the rate of passage can be precisely controlled through the LACs to optimize polarization transfer efficiency. The shuttling from 7 T-8 mT took 648±2.5 ms (see FIG. 3C), a remarkably high repeatability, which is in contrast to conventional pneumatically controlled field cyclers.

Certain embodiments of the disclosed technology incorporate special features to maximize sample fill factor for highly efficient inductive detection, and low-field quantum control through radiofrequency or microwave excitation. For minimum position/velocity control possible clearance to excitation coils at both fields, and low vibration upon motion jerk it is essential that the shuttling rod be aligned perfectly parallel to the magnet over the entire distance of travel. Alignment better than 1 mdeg can be obtained through a series of design implementations. Firstly, the entire shuttling tower (e.g., 80/20 1530-S) containing the actuator, motor and twin carriage is on an XY tunable platform (see FIG. 2A), centering the shuttling rod to the magnet bore with a precision better than 0.25 mm over the 1600 mm travel. Secondly, two novel alignment funnel-shaped guiding stages made of soft teflon are employed at the magnet bore (see FIG. 2F), and NMR probe (see FIGS. 6B-6C). The stages vertically align the structure, and provide additional points of support to greatly reduce vibration. The carbon fiber shuttling rod (e.g., 8 mm diameter, 1.7 m length, Rockwest composites), while soft enough to be guided by the teflon stages, is inherently less prone to vibration due to its low moment of inertia and high strength (e.g., 430 GPa tensile modulus).

Figures 4A, 4B, 4C:
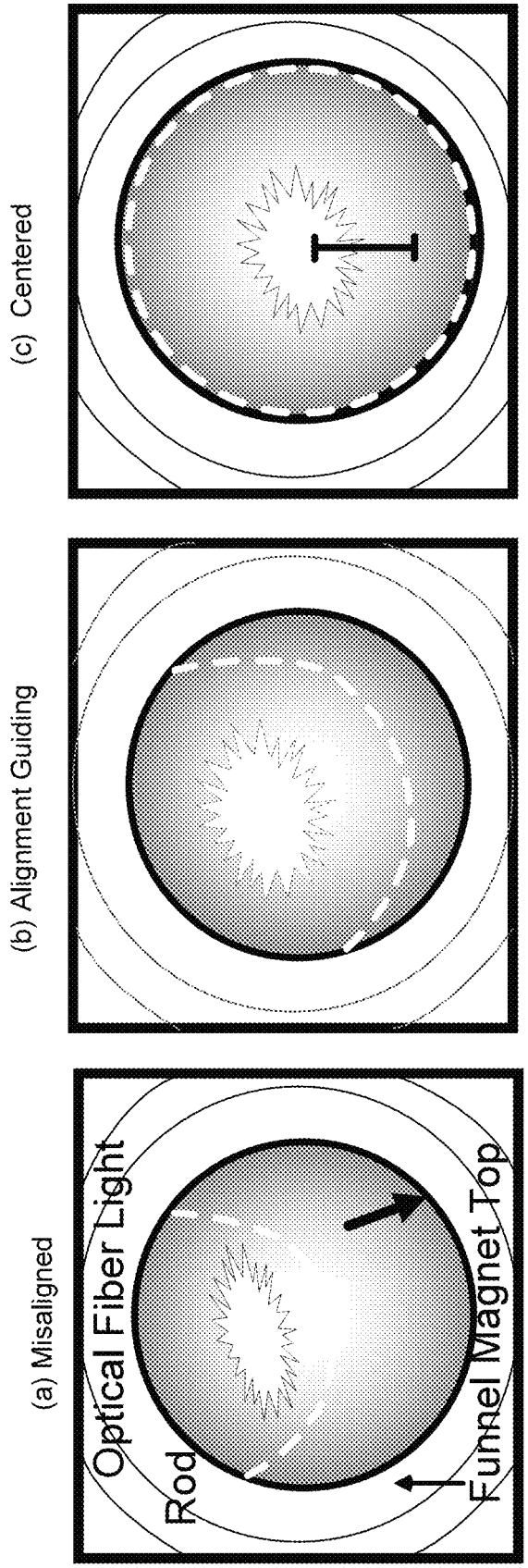
FIGS. 4A-4C illustrate an example of guided self-aligning high-speed shuttling.

FIG. 4 visualizes the guiding process, taken with a camera located in the NMR probe focusing on the teflon guide above it (see FIG. 6B). The rod starts out slightly misaligned but is dynamically guided to be perfectly aligned, the carbon fiber malleable enough to be able to guide into place with no jerk. The funnel guide has a 45-degree taper with an opening of 8.077 mm, ensuring a tight fit with the 8 mm shuttling rod. Overall this ensures shuttling with minimum clearance to the NMR coil and high fill-factors (see FIG. 7).

The sample is pressure-fit to the carbon fiber rod for rapid attachment and detachment. The lower end of the rod contains a ceramic connection for attaching the NMR tube carrying the sample (see FIG. 2C). It can consist of a pair of soft, high temperature modulus, silicone O-rings (e.g., McMaster 1/16 Fractional Width, 0.254" OD). Remarkably, this arrangement proves resilient for fast shuttling with just the simplicity of a hand-tight pressure fit. The diameter of the NMR tube (e.g., Wilmad 8 mm OD, 1 mm thickness) can be selected to match that of the shuttling rod for a seamless joint through the alignment guides.

FIG. 2D details the tube experiments on powdered diamond. A plunger carrying a dielectric mirror is used to isolate the sample to a compact volume. The plunger is fitted with a threaded screw hole for easy fastening access, positioning, and removal. The mirror (e.g., Thor-labs BB1-E02 Broadband Dielectric Mirror, 400-750 nm) is machine ground to the inner diameter of the NMR tube, and provides a double pass for the incoming laser radiation for efficient polarization of NV center electrons.

Figure 5:
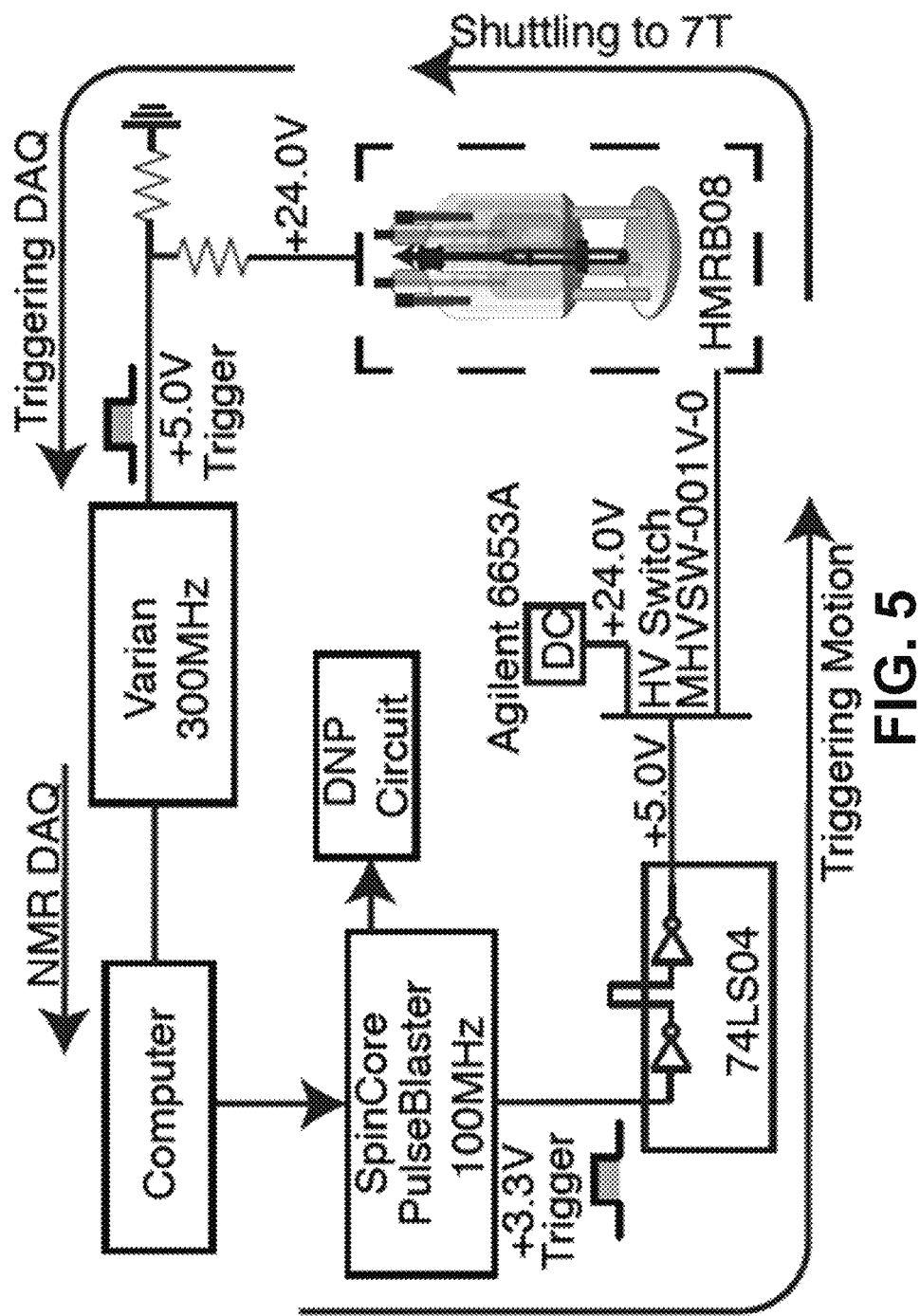
FIG. 5 illustrates an example of trigger sequence for field cycling and detection.
Figures 9A, 9B:
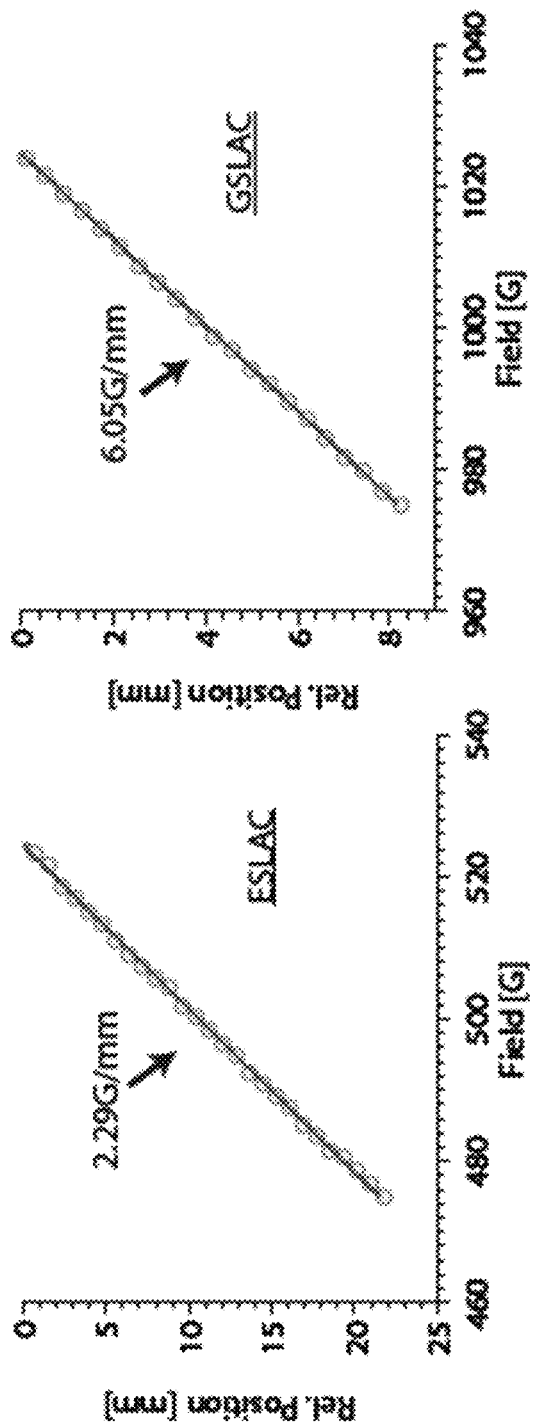
FIGS. 9A-9B illustrate an example of accessing level-anticrossings in diamond.
Figure 10:
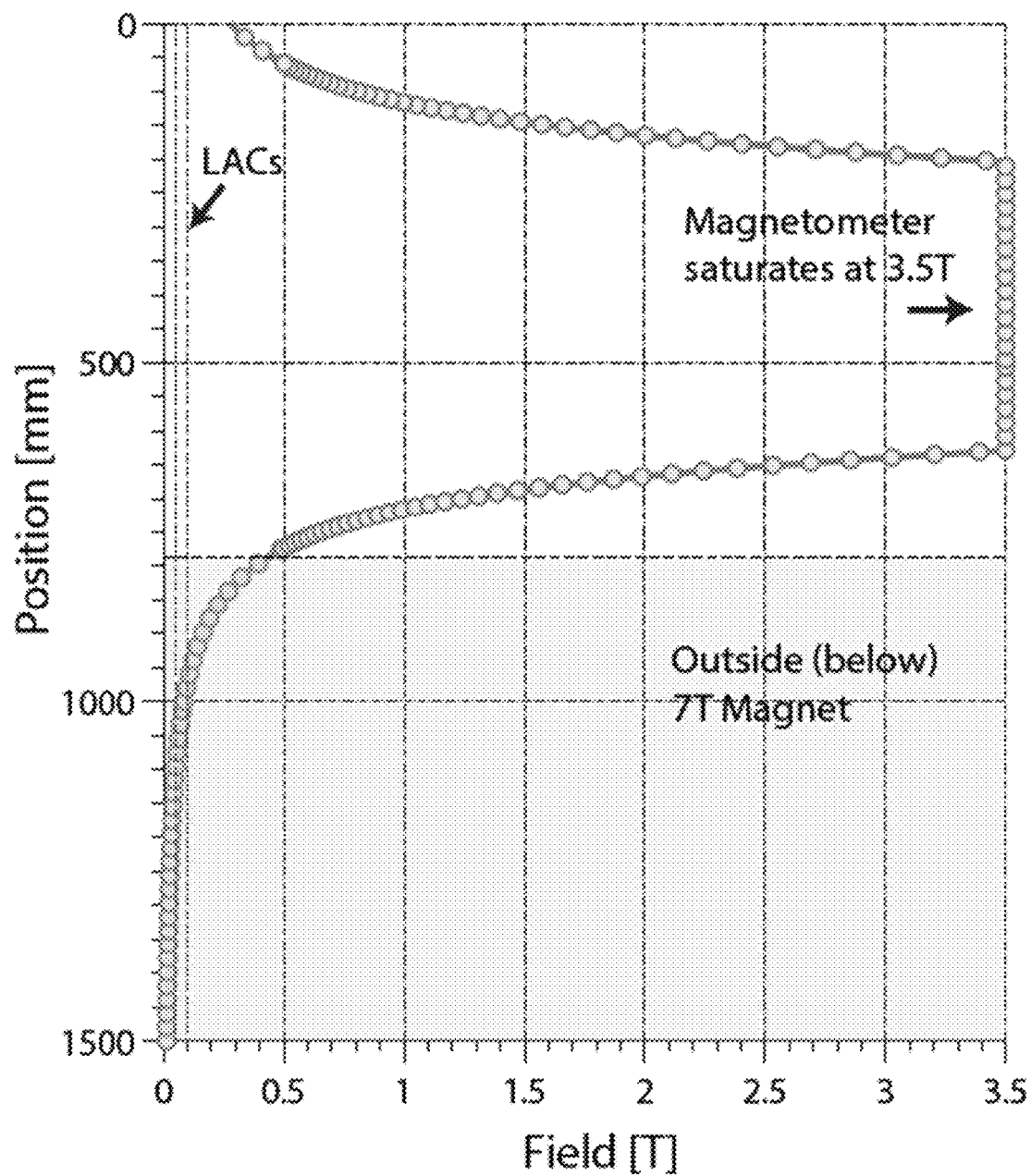
FIG. 10 illustrates an example of a full field map ranging from field inside an Oxford 7 T magnet to the fringe field outside.

Shuttling and inductive detection can be synchronized (see FIG. 5) using a high-speed pulse generator (e.g., SpinCore PulseBlaster USB 100 MHz). The servo motor is triggered to start motion for shuttling with a 24V 10 ms pulse. This is generated by upconverting the 3.3V pulse trigger from the pulse generator to 5V by a TI SN74LS04N CMOS inverter, for example, which then serves as the gate to a high voltage MOSFET switch (e.g., Williamette MHVSW-001V-036V). The MOSFET switch relays the 24V pulse to the servomotor that drives the belt-driven actuator stage to the desired position. Finally, the actuator returns a 24V pulse indicating the completion of motion, which is passed through a voltage divider to trigger the NMR console (e.g., Agilent DD2) to initiate measurement (see FIG. 5), and by which the shuttling jitter can be precisely quantified (see FIG. 3).

Field cycling methods have long been developed to overcome the shortcoming that inductive detection is only operated at one certain field while many phenomena, which can be probed by it, are magnetic field-dependent, for instance, spin relaxation and spin hyperpolarization. There are several approaches of field cycling, including fast (switch) filed cycling, sample shuttling (pneumatic and mechanical).

Fast field cycling exploits specialized power supply and switched-coil to rapidly switch magnetic fields. But it is challenging for the fast field cycling system to exceed 2 T magnetic field, and additionally because of rapid switching of electric current and magnetic hysteresis, the resolution and sensitivity is limited.

Field cycling methods employing sample shuttling have a rich history. They have found a niche for protein relaxometry, where they can reveal important information about intramolecular motion. Compared to conventional pneumatic shuttlers, implementations of the disclosed technology have better repeatability in both shuttling time and shuttling position, and gradual low-vibration motion stop. Pneumatic shuttlers use compressed air to operate shuttling motion, which creates inconstancy on shuttling time. While providing higher speed, compressed air causes vibration on samples when the shuttler starts and stops. 0.1-1 s of time is applied to wait for the shuttler to stabilize, which compromises the advantage of rapid shuttling. On the other hand, the belt driven linear actuator as disclosed herein has a thrust force capacity of 295N, under which platform, a variety of samples can be loaded and measured with high stability. The experiments are stable and reproducible over months of operation.

Devices in accordance with the disclose technology differ from previous mechanical shuttler implementations in certain key areas. Embodiments can employ mechanical sample shuttling, which have advantages over pneumatic shuttling, but unlike the previous works however, the disclosed devices move the sample outside the magnet and into a shield, allowing orders of magnitude wider dynamic range in the field cycling and approachability to more experimental apparatus, such as low field shield and zero filed pulser etc. Since implementations include shuttling towards the ground, it also allows easy access to optical radiation and microwave application, that can be employed for polarization transfer.

Modifications to conventional NMR probe design can be made to accommodate fast sample shuttling (see FIGS. 6A-6C). FIG. 7 visualizes the actual shuttling process at the probe. The probe is designed hollow for shuttling to low fields below the magnet and is constructed out of 12.7 mm thick brass plates for enhanced shielding and structural rigidity. The top plate holds the matching capacitors (e.g., Voltronics AT4HV and AP14) along with the quartz tube inside of which is fabricated a saddle shaped NMR coil (e.g., 9 mm×11 mm Technical Glass Products). The probe accommodates both split coils (see FIG. 7) as well as the current saddle shaped one (similar to FIG. 8C). The teflon funnel at the top (see FIG. 6B) allows for the rod to self align allowing high sensitivity inductive detection with fill factor >0.57.

Certain embodiments can include fabricating saddle coils for NMR detection that are compatible with shuttling, yet optimized to the sample to provide large fill factors. The coils are wrapped on a Quartz tube matched to the tube being shuttled such that the sample tightly fills the entire coil volume. The coils are fabricated by cutting them out of flexible adhesive copper foil (e.g., Venture Tape, thickness 31.75 µm) (see FIG. 8C) using an inexpensive vinyl cutter (e.g., Silhouette Cameo2) in 17 seconds and 1.5 mm cutting depth, for example. The RF coil in the probe has 8.64 mm 110° windows and track width of 1.02 mm with 0.61 mm spacing. After printing, excess copper around the coil was carefully removed and contact paper (e.g., Circut Strong-Grip Transfer Tape) was applied on top to maintain the coil shape. When inserted into the quartz tube, the inside of the tube was coated with water to prevent the coil from adhering while positioning to a slit for the leads to pulled through. A heat gun was used to release the contact paper and adhere the coil to the wall of the tube. The fabricated coils for $^{13}$C NMR had an inductance of 0.28 uH and Q factor of the ~20 at 75.03 MHz.

The low-field center at the lower end of the field cycling platform consists of a magnetically shielded volume (see FIG. 2E). The shield is constructed by concentric layers of stress annealed iron (e.g., NETIC S3-6 alloy 0.062" thick, Magnetic Shield Corp.) and mu-metal (e.g., TwinLeaf MS-1), with the iron on the outside due to its high saturation, and mu-metal on the inside due to its high permeability (over $10^6$ with 4 layers). In combination, with 3 layers of iron and 4 layers of mu-metal, we can achieve a lower field center of approximately MT. The shields are positioned on secured sliding rails under the magnet (see FIG. 2E) to contain upward forces. In practice, the low-field shielding can be customized to suit the target field desired in experiments, reach for instance low fields (1-10 mT) for DNP experiments, ultra-low fields (<1 µT) for relaxometry, and zero fields <1 nT for experiments.

In several embodiments of low-field optical polarization transfer from NV centers to $^{3}$C nuclear spins in diamond, an iron shield is employed. Laser light is irradiated from the bottom of the test tube holding the sample (see FIG. 8). Additionally, a stub loop antenna of diameter 8 mm applies swept-frequency microwave radiation that performs the polarization transfer (FIG. 1).

In some embodiments, a cryogenic system was constructed for sample fast freezing to increase low field T1. This allows for investigation of the field dependence of the T1 of frozen liquids as well as its applications. The solid form of various substances have relaxation times orders of magnitudes larger. For instance, pyruvate which was demonstrated as an important probe of cellular glycolysis in cancer, has T1 relaxation time at magnetic fields greater than 7 T of less than 49 seconds at 310K, compared with 3200 seconds 4.2K. This increase in T1 can be crucial for potential hyperpolarization transfer outside a hyperpolarized substance and into an external frozen liquid. In the solid state, longer relaxation time will enable extending the duration (and therefore the amount) of polarization build up as well as the diffusion of the polarization into the solid liquid. Longer T1 will also enable quantum applications.

Figure 11A:
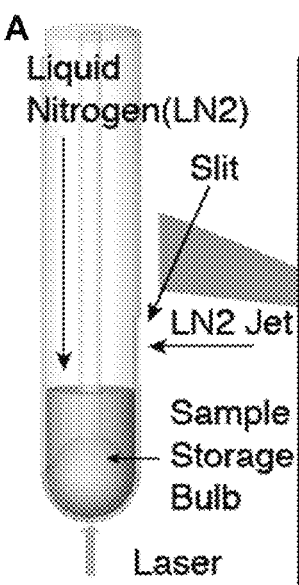
FIGS. 11A-11C illustrate an example of a cryogenic system in accordance with certain implementations of the disclosed technology.
Figure 11B:
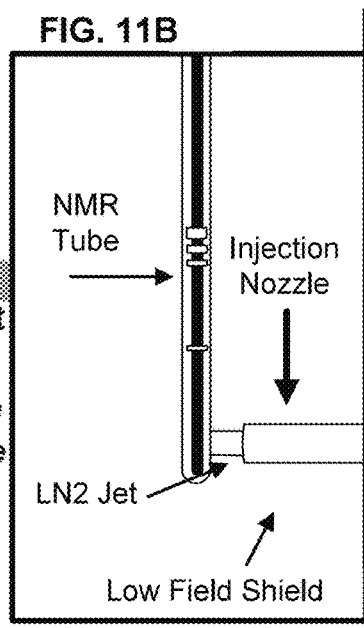
Figure 11C:
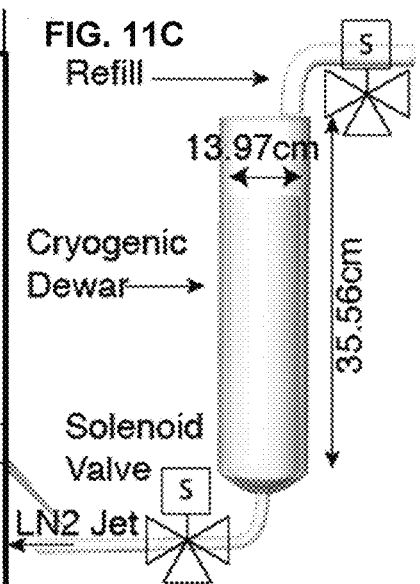

FIG. 11 describes an example of the setup. A uniquely designed cryogenic system applies a consistent jet of cryogenic liquid, the use of which cools the sample to 77K (liquid nitrogen temperature) within 3-4 seconds, and has the potential to reach 4K (liquid helium temperature). A dewar that has two openings stores cryogenic liquid and creates pressure for even liquid flow. The top opening is for (re-)filling by external nitrogen source, and the bottom for injecting liquid into a quartz nitrogen nozzle to generate a jet. Both inlet and outlet are regulated by two Solenoid Valves individually (e.g., Asco 1/4 Cryogenic Solenoid Valve, 7/32 Orice Dia., 24 VDC), which can be triggered indirectly by the Pulse Blaster and respond within 1 ms to ensure synchronization. Laser irradiation and cryogenic cooling can be coordinated to occur simultaneously. In the NMR tube, a glass bulb containing the sample is immersed in the cryogenic liquid, forming a low temperature bath to freeze the sample. As shown in FIG. 11A, a fine slit on the NMR tube is created to let cryogenic liquid inject in. The liquid remains in the NMR tube for more than 30 s with only is injection, during which period the temperature in the tube remains stable even with laser irradiation.

Recently, the first mechanism of optical DNP in diamond particles, hyperpolarizing $^{13}$C nuclear spins in microdiamonds was developed, opening the door to the optical hyperpolarization of liquids brought in contact with these high surface area particles. The embodiments here harness the remarkable versatility of this DNP mechanism to develop a compact, along the size of a laptop computer, inexpensive in the range of under $3000, solid-state "nanodiamond hyperpolarizer" that is easily interfaceable with any existing NMR/MRI system both at low and high fields. It is capable of hyperpolarizing $^{13}$C nuclei in diamond micro- and nanoparticles diamond, in the range of 5-200 nm size, to approximately 0.4% bulk polarization in under one minute. The ease of construction and low cost of the device opens several avenues for harnessing the biocompatible surface-functionalized nanodiamonds as MRI tracers, as demonstrated here, besides highlighting its strong potential for the optical hyperpolarization of liquids.

$^{13}$C hyperpolarization is generated by the simultaneous and continuous application of laser irradiation that polarizes the NV center to the $m_s=0$ sublevel and frequency swept microwave (MW) irradiation that transfers it to the $^{13}$C nuclei, at low background polarizing fields $B_{pol}$=1-30 mT. At these fields, the embodiments work in the regime where the MW excitation is nuclear spin level selective, for example $\Omega_e \ll w_L < A$, where $\Omega_e$ is the electron Rabi frequency, $w_L=\gamma_n|B_{pol}|$ is the nuclear Larmor frequency, and A is the hyperfine coupling to the $^{13}$C nuclear spin in the lattice. The MWs are set to sweep the entire NV ESR spectrum, driving successive rapid adiabatic passages (RAPs) between the $m_s=0$ and $m_s=\pm 1$ manifold and back, hyperpolarizing the $^{13}$C nuclei in a direction solely dependent on the direction of the MW sweep. Indeed, the $^{13}$C polarization is aligned or anti-aligned with $B_{pol}$ depending on whether the MWs are swept from low-to-high or high-to-low frequency respectively. Technologically however, it is the remarkable and somewhat surprising aspects of the mechanism that facilitate miniaturization of the hyperpolarizer: the laser excitation required is of a wide wavelength range, and low power ($\approx 5$ mW/mm$^2$) and can be produced by low-cost LEDs; the MW power is exceeding low ($\approx 50$ mW/mm$^2$), with a frequency range and power comparable to commercial Wi-Fi routers; and the low polarizing field 1-30 mT can be produced by simple permanent magnets with no requirements for sample alignment nor constraints on field homogeneity.

The discussion now turns to the implementational flexibility. The embodiments work at low polarizing fields chiefly to mitigate the strong inhomogeneous broadening, by $B=2\gamma_e|B_{pol}|$, of the NV center electronic spectrum stemming from the orientation dependence of the NV center resonance frequencies, and the fact that all NV orientations are sampled in a random powder. The relatively narrow resulting spectral widths, typically B=100-700 MHz around $\approx 2.9$ GHz, can be coherently swept over by MWs generated by any of the plethora of inexpensive broadband sources and amplifiers in this range (S-band). The optimal $B_{pol}$ is determined by an interplay between technical ease of MW frequency sweeps at lower fields, and the longer spin lifetimes $T_{1n}$ at higher fields. The $^{13}$C hyperpolarization builds up rapidly and approaches $\approx 0.4\%$ usually in under 60 s of optical pumping, which corresponds to a signal enhancement of $\approx 400$ times with respect to the thermal Boltzmann polarization at 7 T. Field inhomogeneity goes only to broaden the ESR spectrum, and does not significantly alter the DNP enhancements. Hyperpolarization occurs along the local $B_{pol}$, which need not necessarily align with the detection field, since the sample transfer is, to a good approximation, adiabatic. Moreover, since there are no field alignment requirements, the DNP can be performed in the fringe field of conventional NMR/MRI superconducting magnets.

In one embodiment, experiments were performed at three different fringe field spots of an 800 MHz (Bruker Avance) NMR magnet, obtaining comparable DNP enhancements independent of location. Indeed, the compact size of the device allows easy interfacing with detection magnets, and samples can be accessible both from the top and bottom of the device.

The low requirement for microwave power is a consequence of a need to maintain nuclear selectivity in the RAP transfer, but this also proves to be a significant technological advantage, allowing one to harness inexpensive GaN HEMT transistors developed for the WiMAX band. MWs can be delivered by means of a simple broadband stub antenna, without the need of a cavity or other resonant structures. The ubiquitous availability of voltage controlled oscillator (VCO) sources in the 2-4 GHz band, and their prevalence as chip-scale components, simplifies miniaturization. This contrasts with conventional DNP where sources, both gyrotrons and solid-state ones, are significantly more expensive and substantial resources are required for MW amplification and delivery. The optimal MW frequency sweep rates required for polarization transfer are set by adiabaticity constraints of the RAPs, and are typically in the 50-200 Hz range. This allows use of exceeding simple microcontroller based sawtooth voltage generators, which when interfaced with the VCOs produce the desired MW sweeps.

Indeed, the ease of construction enables the cascading MW sweeps from several (say N) VCO sources simultaneously to enhance the efficiency of polarization transfer. This is because the NV electrons rapidly repolarize optically in $t_{repol} < 100$ μs, while the slow MW sweeps bottleneck the DNP enhancement F produced by a single VCO. Cascaded sources can provide multiplicative gains $\varepsilon \to N\varepsilon$, where N is bounded only by limits set by the homogeneous linewidth of the electron spectrum, $N \leq B = /\Delta f$. Finally, since the entire spectrum produces the identical hyperpolarization sign, any part of it can be swept to produce DNP enhancements, and there is little need for exact frequency matching of the sweep bands.

Optical pumping, used to polarize the NV centers, can be of a wide wavelength range, any visible excitation $\lambda \approx < 575$ nm). Importantly, the DNP mechanism requires that the illumination power be low $\approx 5$ mW/mm$^2$. This is because one needs to ensure that the NV centers are not significantly repolarized during each RAP polarization transfer event. There are almost no requirements on the mode quality, or the alignment of the beam if the particles are uniformly illuminated. Moreover, the excitation is applied completely in cw-mode, without the need for pulsing or any synchronization circuitry. Consequently, the hyperpolarizer can be built from compact LED sources widely available, and the light delivered directly from the source with no intervening optics. Indeed, several embodiments may have the illumination occur by means of optical fibers. The use of IR-visible coatings can potentially allow in-vivo excitation and DNP of the particles.

Room-temperature DNP can be carried out with the diamond particles both dry as well as suspended in solution. There is a remarkably wide range of solutions in which the diamonds are hyperpolarizable, including common solvents and biologically relevant fluids.

The versatility, ease of construction and operation of the nanodiamond hyperpolarizer open compelling possibilities especially for biosensing imaging modalities constructed out of optically hyperpolarized, surface functionalized, diamond particles. This may be in theranostics both in-vivo and in-vitro. From a technological standpoint, the device itself can easily be further miniaturized into palm top hyperpolarizers.

In this manner, the embodiments demonstrate an inexpensive compact room-temperature diamond particle hyperpolarizer. The device is extremely easy to construct and operate, and can be interfaced with almost any existing NMR system. The large $^{13}$C polarizations, and high particle surface areas ($\approx > 6700$ mm$^2$/mg for 100 nm particles), can be potentially exploited to optically hyperpolarize contacting liquids. There may be immediate applications of the device for dual modality optical and MRI imaging with fluorescent diamond particles, opening compelling possibilities for disease detection and targeting in-vivo. The device may have an interface that allows it to connect with one or both of an existing NMR machine or an MRI machine.

In one embodiment, diamond particle hyperpolarization was carried out in a stand-alone device at room-temperature, composed from nonmagnetic solid-state components and requiring zero user maintenance. The embodiment used a modular design that allows a compact and rapid assembly of the various components. The most striking feature was its small footprint (12×10×10 in.), and light weight (<10 lb), making it ultraportable, and compatible with any NMR spectrometer. Indeed, this may be the smallest reported hyperpolarizer across all platforms, a testament to the technological ease of optical DNP at low fields.

Figure 12:
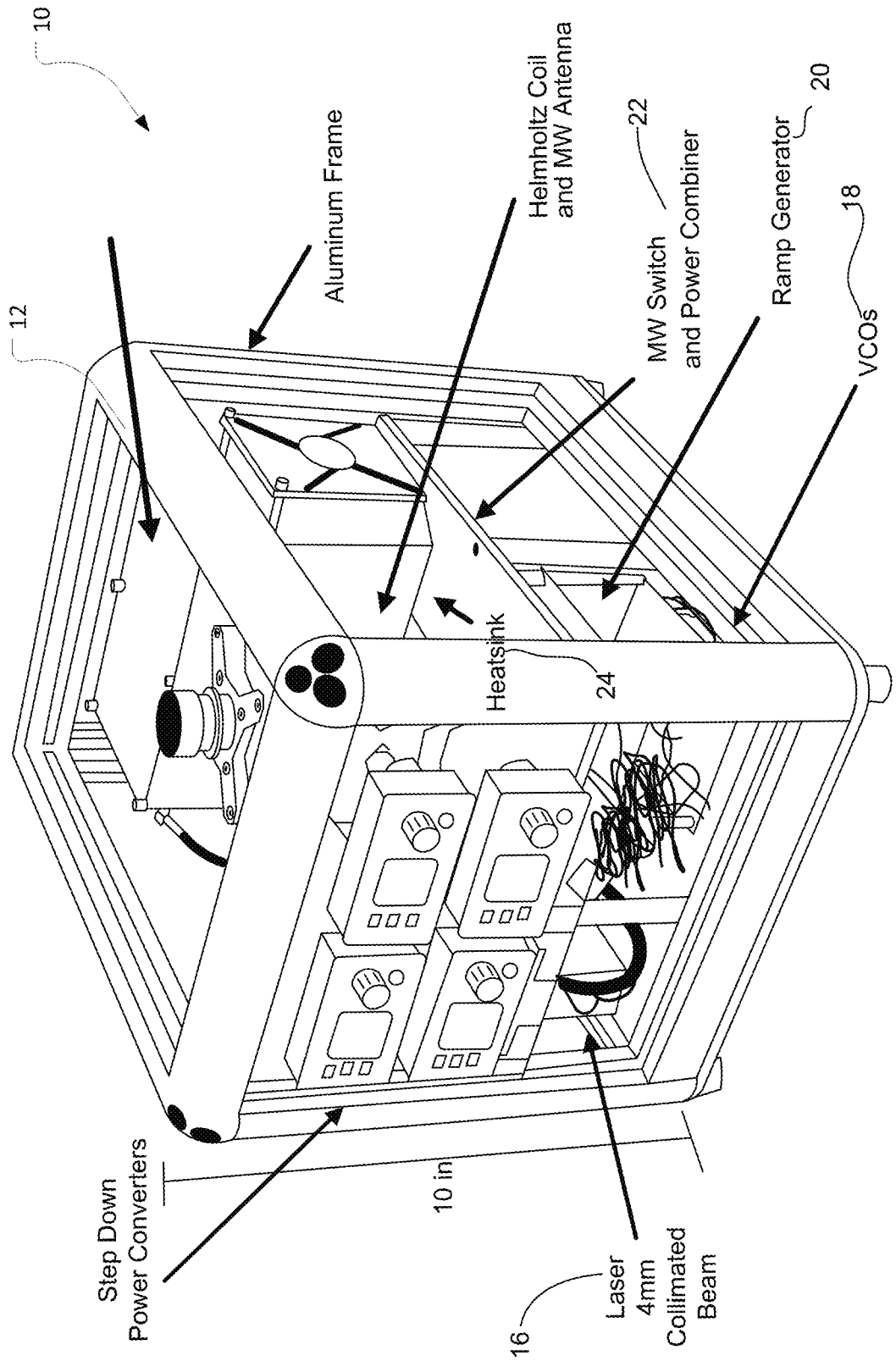
FIG. 12 illustrates a first view of an embodiment of a desktop nanodiamond hyperpolarizer.
Figure 13:
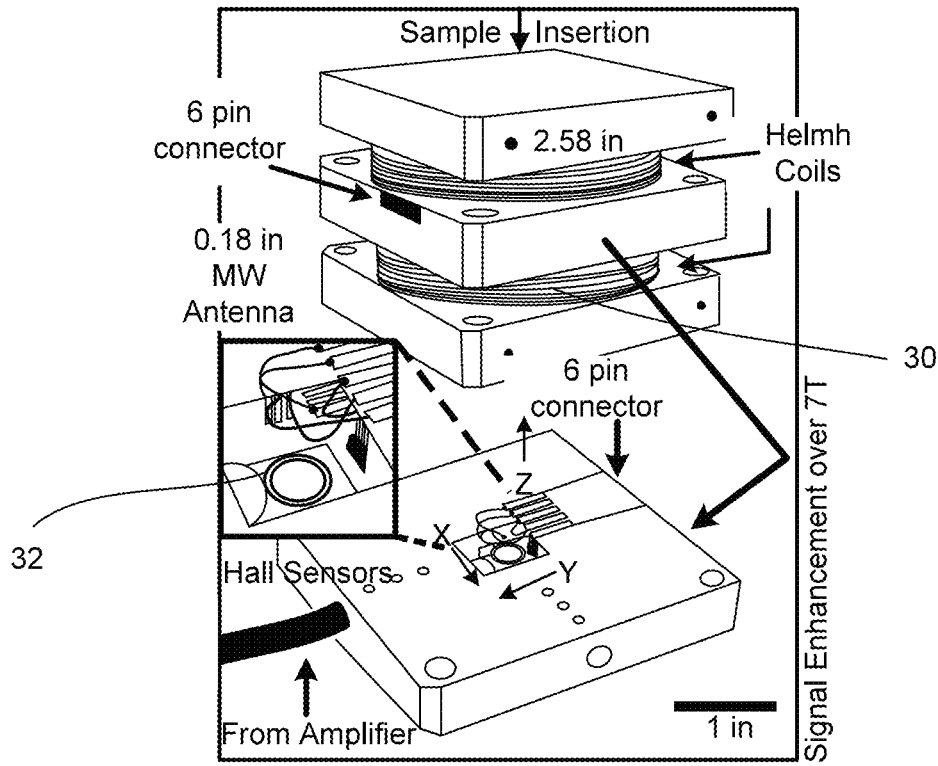
FIG. 13 illustrates a second view of an embodiment of a desktop nanodiamond hyperpolarizer.

FIG. 12 illustrates an embodiment of a desktop diamond particle hyperpolarizer 10. One should note that this is just one embodiment and is not intended to limit implementations in any way. A rigid aluminum chassis 12 supports three distinct modular blocks: optics, MW sweep generation, and a sample holder, shown in FIG. 13, that contains the diamond particles to be hyperpolarized. In the embodiment of FIG. 13, the sample resides adjacent to a Helmholtz coil 30 next to the microwave antenna 32. The densely packed and doubled-sided design supports easily customizable modalities for sample placement and removal. For instance, the device can contain a hollow bore to allow shuttling of the sample into a high field NMR magnet.

Referring to FIG. 12, this embodiment has a laser diode or other laser source 16 that is directed at the sample. The sample is then irradiated with microwaves. In this embodiment, the microwave source comprises at least two voltage controlled oscillators 18 under control of a ramp generator 20. The microwave signals are power combined by power combiner and microwave switch 22. The chassis also has a heat sink 24 to disperse heat from the various energy sources.

Figure 14:
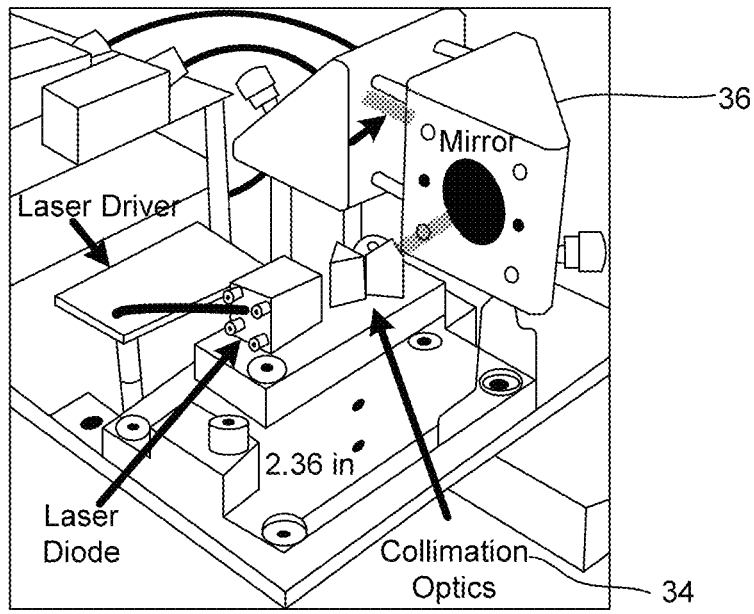
FIG. 14 illustrates a third view of an embodiment of a desktop nanodiamond hyperpolarizer.

The specific embodiments here employ a miniature 1 W 520 nm diode laser in a feedback loop with an integrated thermoelectric cooler for adequate thermal control. FIG. 14 shows that very few optical components are required: an aspheric lens and a set of anamorphic prisms 34 collimate the beam to a circular 4 mm diameter. Two mirrors 36 redirect the beam towards the sample, typically irradiating it from below, although this is customizable.

Figure 15:
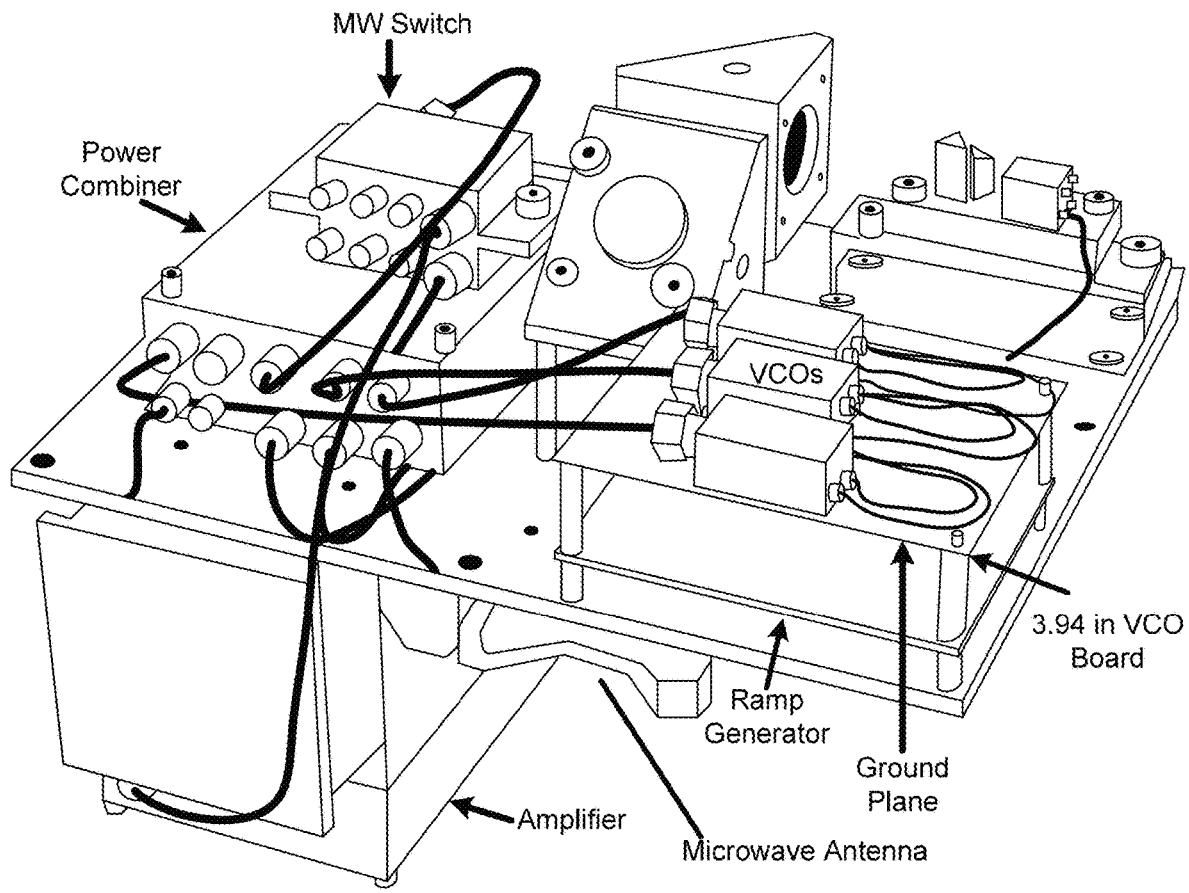
FIG. 15 illustrates a fourth view of an embodiment of a desktop nanodiamond hyperpolarizer.

Microwaves are generated by miniature voltage controlled oscillator (VCO) sources 18. Frequency sweeps are produced by controlling the VCO frequency by a homebuilt quadruple channel voltage ramp generator 20 in FIG. 12 controlled by a PIC microprocessor. FIG. 15 shows the connected VCOs 18 mounted on a copper sheet that serves as a good ground plane. Given the relatively slow MW sweeps required, d>=20-60 MHz/ms, translating to sweep times of 10-50 ms for the typical sweep bandwidths B=100-700 MHz, the 50 kHz clock speeds of the microprocessor provide sufficiently fast control for the sweep circuitry.

Figure 18:
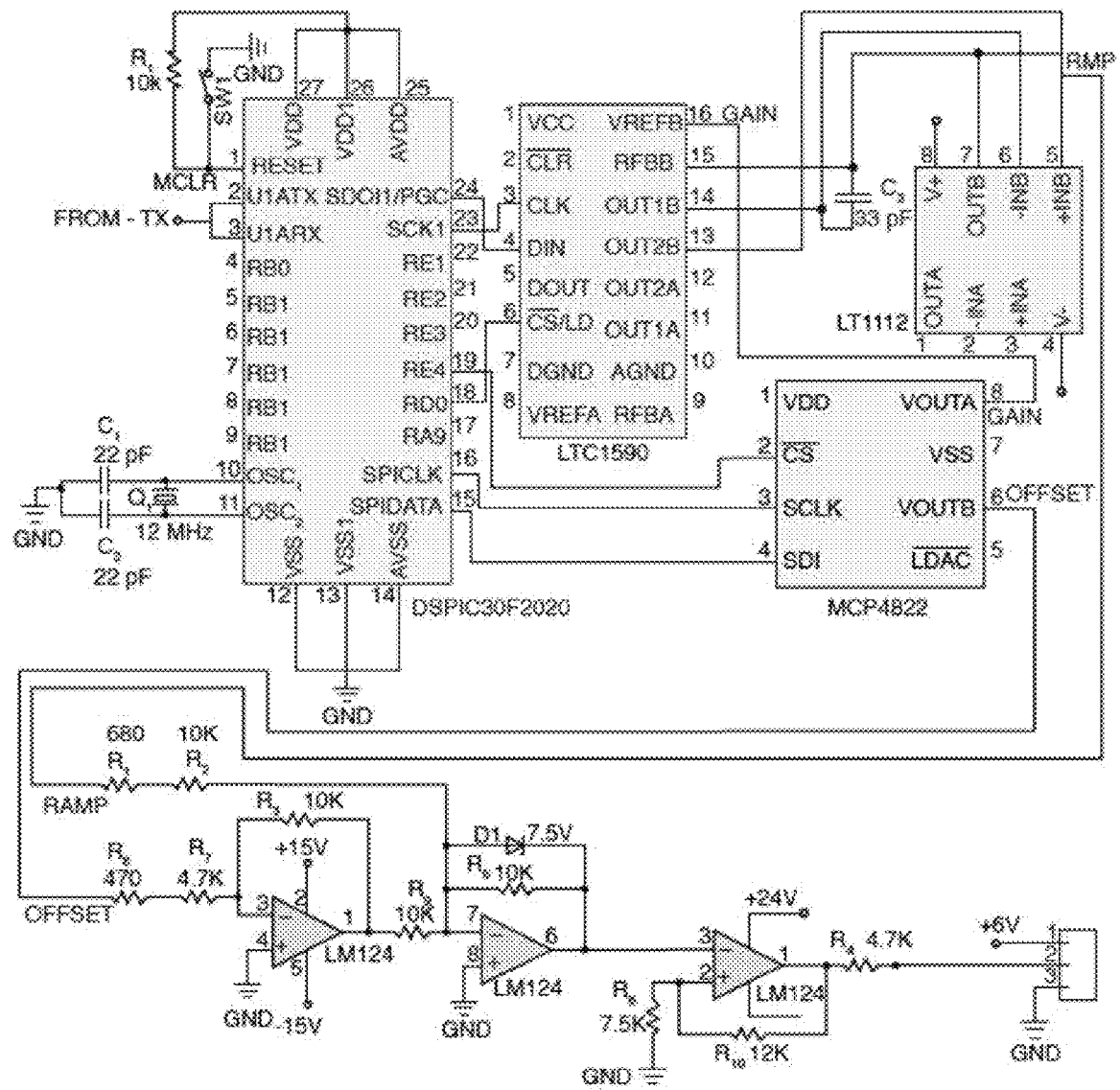
FIG. 18 illustrates an embodiment of a ramp generator circuit.

FIG. 18 illustrates a diagram of the ramp generator circuit. In this embodiment, the circuit employs dual multiplying digital-to-analog convertors to generate the sawtooth voltage ramps. The sweeps from the individual sources are time-cascaded, generating effective a MW frequency comb, discussed in more detail below, that sweeps different parts of the NV ESR spectrum at once. This allows multiplicative gains in the obtained DNP enhancements. The VCO outputs are power-combined and delivered to a low-cost amplifier that transmits the microwave irradiation to the sample via a stubbed loop antenna (5 mm diameter). The MW powers required are extremely low, estimated to be below 1 W.

The diamond particle sample is placed at the confluence of the applied laser and microwaves, and in a weak polarizing field. For several experiments, it is most convenient that the natively fringing fields of the NMR/MRI detection magnets are employed for this task. Alternatively, as described in FIG. 13, the embodiments here employ a single axis Helmholtz coil (15 turns, 10 layers, 0.8 mm diameter) mounted around the sample, generating 15 mT fields with ≈6 A of current, and with minimal heating. The coil also helps in the hybrid scenario to supplement magnet fringe fields. A small Hall sensor is placed near the sample, and helps for the in-situ measurement of the field, and a simple feedback loop can match the field with any desired value.

Figure 16:
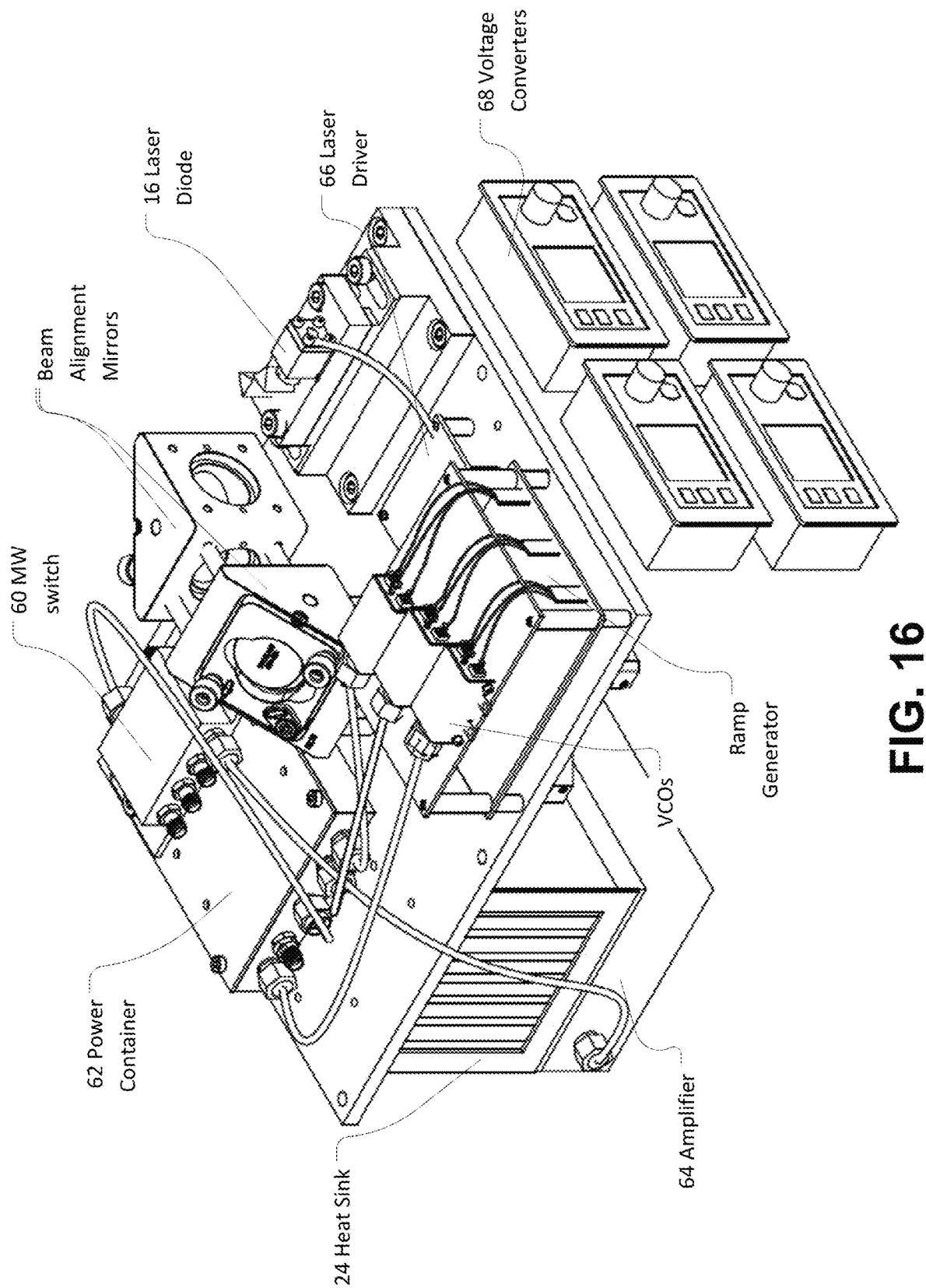
FIG. 16 illustrates an isometric bottom view of an embodiment of a desktop hyperpolarizer.
Figure 17:
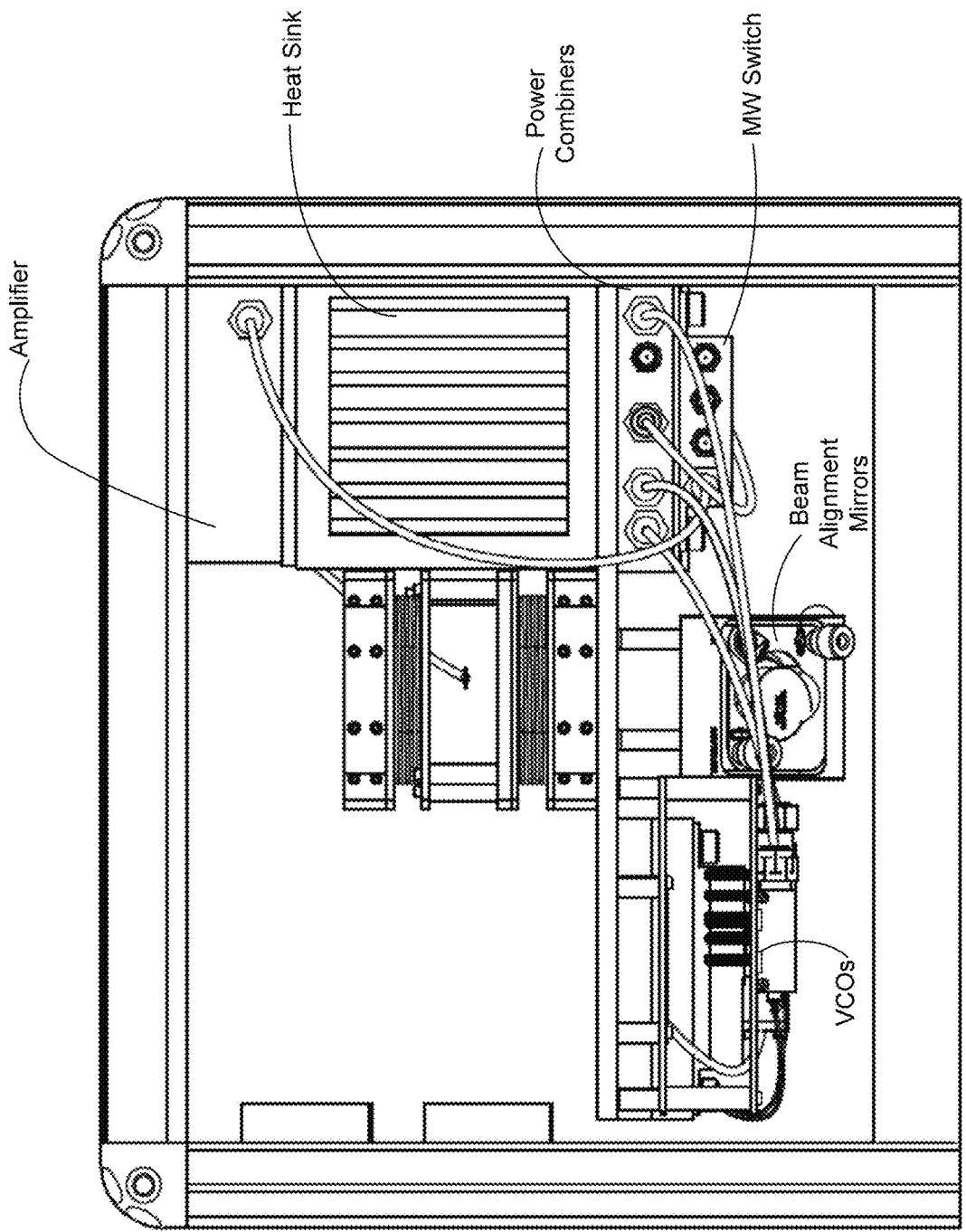
FIG. 17 illustrates a side view of an embodiment of a desktop hyperpolarizer.

FIGS. 16 and 17 views of an embodiment of a desktop hyperpolarizer. In FIG. 16, one can see both the microwave switch 60 and the power combiner 62. An amplifier 64 resides adjacent the heat sink 24 opposite the ground plane. The VCOs 18 are connected to the ramp generator circuit 20 and the laser diode 16 has a laser driver 66. Voltage step-down converters 68 to simplify power input to the component parts. FIG. 17 illustrates another view to allow for a better understanding of the layout of the hyperpolarizer.

Figure 19:
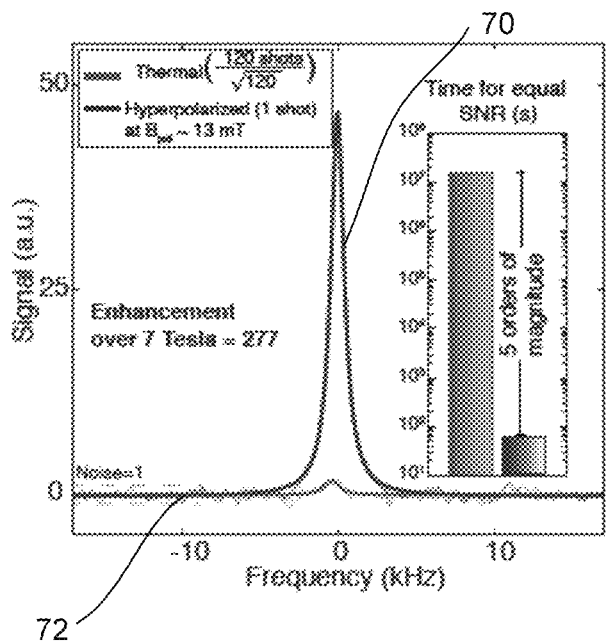
FIG. 19 illustrates a graph of results from an embodiment of dynamic nuclear polarization using a desktop nanodiamond hyperpolarizer.

In one embodiment, the results of which are shown in FIG. 19, the device was employed to perform DNP on a 200 m diamond particles. $^{13}C$ signals were measured by rapid transfer to a 7 T NMR magnet at $B_{pol}$=13 mT. The line with the single spike 70 shows a Boltzman signal at 7 T, averages 120 times over 7 hours. The lower line 72 is a single shot DNP signal obtained with 60 s of optical pumping, enhanced by 277 over the 7 T thermal signal (enhanced 149153 times at $B_{pol}$). The signals have their noise unit-normalized for clarity. Hyperpolarization leads to over 5 orders of magnitude gains in averaging time.

Figure 20:
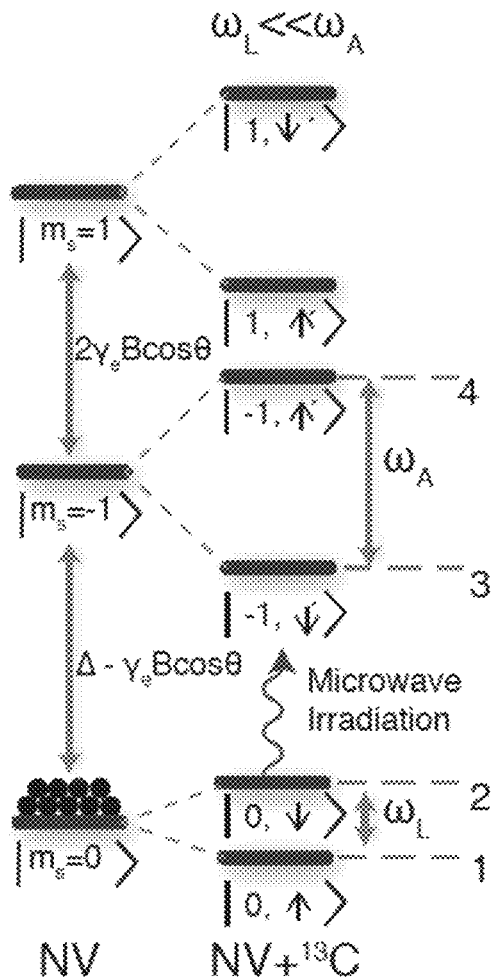
FIG. 20 illustrates a graphical representation of a mechanism of polarization transfer.

FIG. 20 illustrates an example of the mechanism of polarization transfer. Energy levels of a NV electron and $^{13}C$ nuclear spin hyperfine-coupled to it with strength $\omega_A$, at low field regime where nuclear Larmor frequency $\omega_L \ll \omega_A$. The NV center orientation is assumed at angle $\vartheta$ to the field $B_{pol}$.

Figure 21:
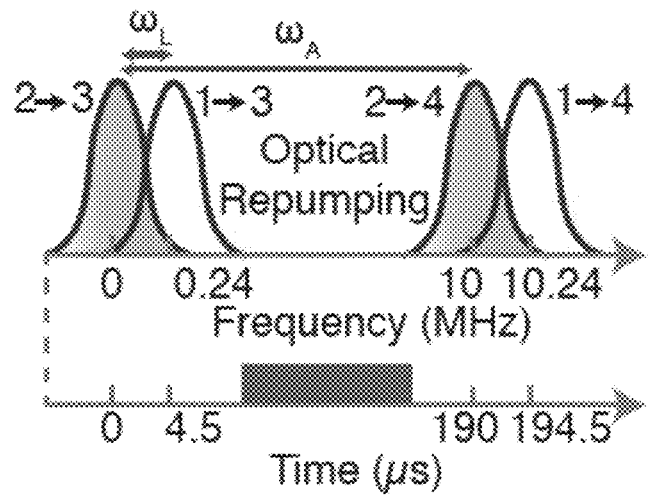
FIG. 21 illustrates an example of sweeping microwave irradiation.

FIG. 21 illustrates an example of the sequential excitation caused by sweeping microwave irradiation. This leads to a series of transitions, shown here for the $m_s=-1$ manifold. There is a time delay between the successive excitations, shown assuming $\omega_A$=10 MHz and a sweep rate of 52 MHz/ms, allowing NV repolarization between the systems.

Figure 22A:
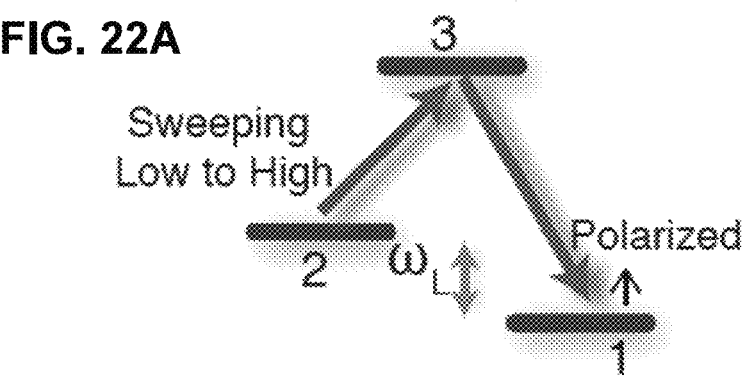
FIGS. 22A-22B illustrate two rapid adiabatic passages.
Figure 22B:
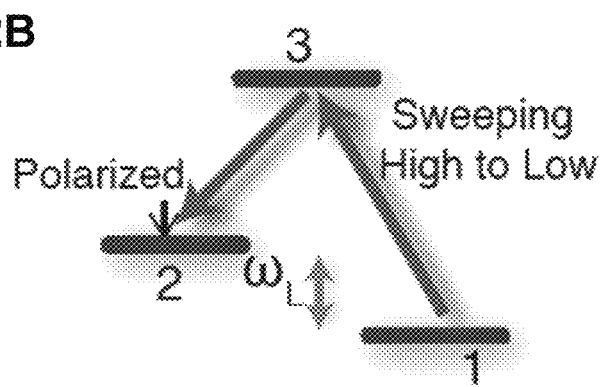

FIGS. 22A and 22B together illustrate two rapid adiabatic passages allow the shuffling of $^{13}C$ population through the system, allowing hyperpolarization in a direction that is only determined by the MW sweep direction.

In this manner, a portable dynamic nuclear polarizer is provided. It has a relatively small size, is lightweight and inexpensive, especially when compared to the rather large systems in use today. This uses for such a system include many different applications, including in accelerated chemical analysis such as may be used by pharmaceutical companies or other entities desiring to test substances, or in conjunction with MRI machines to make brighter, faster images with low signal backgrounds. In particular we envision several applications in accelerated tumor detection and cardiac angiography via the use of hyperpolarization generated from the polarizer device.

As discussed above, one method employed in the above hyperpolarizer involves using frequency combs in the microwave irradiation. While the discussion below relates to hyperpolarizing diamond powder, one should note that it is applicable to many different types of substances.

Dynamic nuclear polarization (DNP), which is the ability to polarize (cool) nuclear spins to a spin temperature far lower than Boltzmann levels—has emerged as a technological breakthrough that serves as the starting point for a wide-range of applications, including signal enhanced spectroscopy and imaging and for state initialization in quantum information processing and metrology. Indeed, magnetic resonance (NMR and MRI) signals from hyperpolarized nuclear spins can be enhanced by several orders of magnitude allowing enormous gains, often greater than million-fold, in experimental averaging time. This has opened avenues for the sensitive probing of phenomena, species, and surfaces, whose detection would otherwise have remained intractable.

In its simplest manifestation, DNP involves the use of electrons whose polarization is transferred to the nuclear spins via microwave irradiation, allowing a polarization enhancement $\varepsilon \approx \gamma_e/\gamma_n$, where $\gamma_{e,n}$ are the gyromagnetic ratios of the electron and nuclear spins respectively. Thermal contact between the electron and nuclear spin reservoirs is achieved via the applied microwaves. Precise energy matching between the reservoirs allows the optimally rapid rate of polarization transfer $\alpha|A|$, the hyperfine coupling between the electron and nuclear spins. The NOVEL pulse sequence typifies this where energy matching in the rotating frame is achieved by equalizing the electron Rabi frequency $\Omega_e$ and nuclear Larmor frequency $\omega_L = \gamma_n B$ (at magnetic field B), at the Hartmann-Hahn condition $\Omega_e = \omega_L$. However, several common (e.g. Nitroxide-based) electron polarizing agents are spin >1/2, and anisotropy leads to severely inhomogeneously broadened electronic linewidths, which scales with the applied field, can be as broad as 1 GHz at high fields (>7 T). Unsurprisingly, precise energy matching to the nuclei is then challenging to achieve. Indeed, DNP traditionally has relied largely on cw-microwave techniques including solid, cross-effects and thermal mixing, where only a part of the broad electron spectrum directly contributes to the obtained enhancement.

In principle however, significant gains in polarization enhancements can be gained by exploiting the full broad electron linewidth for DNP via more sophisticated quantum control on the electron spins, whereby every electron "packet" directly contributes to the DNP process. Since savings in experimental time scale $\alpha\varepsilon^2$, methods to increase hyperpolarization efficiency will directly translate to dramatically accelerated spectroscopy and imaging. Indeed, a surge in recent interest in such control techniques has been fueled by advances in instrumentation (sources and synthesizers) that enable the rapid and coherent manipulation of electrons at high fields. Particularly attractive amongst them is the use of frequency or field swept techniques, such as those using integrated solid effect (ISE), that are suited to exploiting the wide electron bandwidth while only requiring modest microwave power.

Figure 23:
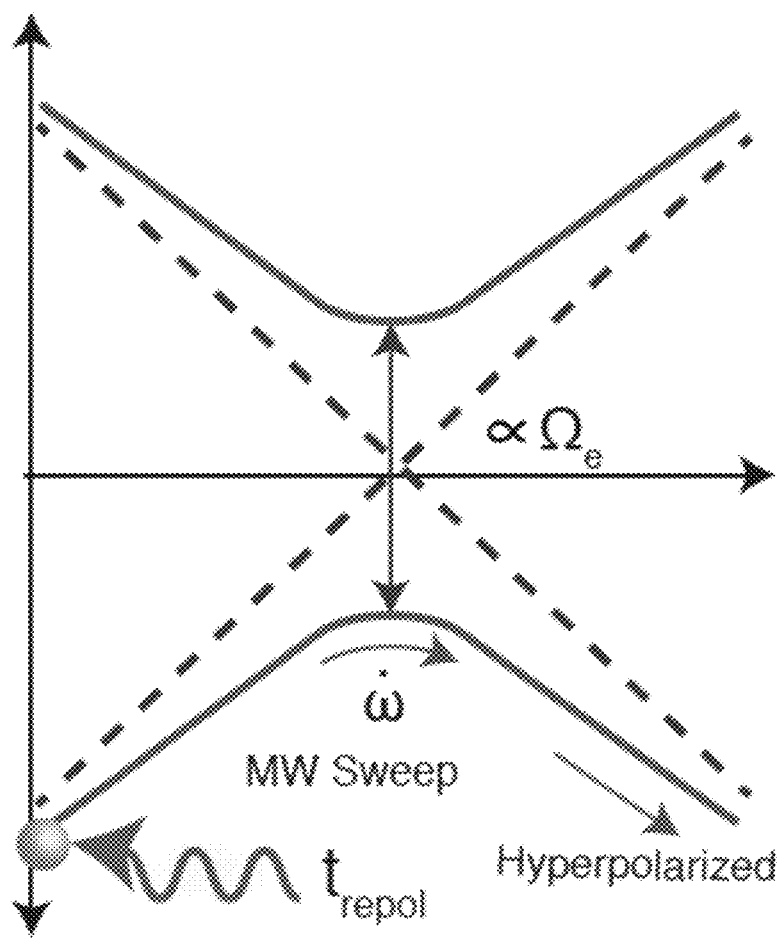
FIG. 23 illustrates a representation of hyperpolarization processes via a frequency/field swept technique.

The DNP process underlying these techniques can be described as traversals of a level anti-crossing (LAC) in electronuclear dressed basis shown in FIG. 23. Polarization transfer occurs via Landau-Zener (LZ) tunneling, the onus of thermal contact being placed on maintaining adiabaticity during the sweep. The transfer efficiency is given by the tunneling probability, $\varepsilon \alpha \exp(-\Omega_e^2/\dot\omega)$, where d is the sweep rate and $\Omega_e$ sets the effective energy gap. Despite harnessing the full electron linewidth, the frequency sweeps are often slow, and the requirement of adiabaticity sets bounds on the rate of polarization transfer. To illuminate this in more detail, for purposes of discussion assume an inhomogeneous electron linewidth $\beta$, leading to a single traversal time $T = \beta/\dot\omega \approx \beta/\Omega^2$. However, each electron frequency packet has repolarized within a time $t_{repol} \lesssim T_{1e} \ll T$, and is available to be employed again for DNP transfer, but instead must wait the full-time period T when the subsequent sweep leads to next polarization transfer event. The nuclear polarization is proportional to the total number of sweeps Tin/T; and the slow sweeps set a bottleneck on the DNP process, since an increasing bandwidth $\beta$ leads to a longer period T. For instance, for the typical case of TEMPO at 5 T, $\beta = 600$ MHz and considering $\Omega_e = 10$ MHz, T=60 ms, which far exceeds the inherent repolarization time, $T \gg T_{1e} \approx 1$ ms.

Figure 24:
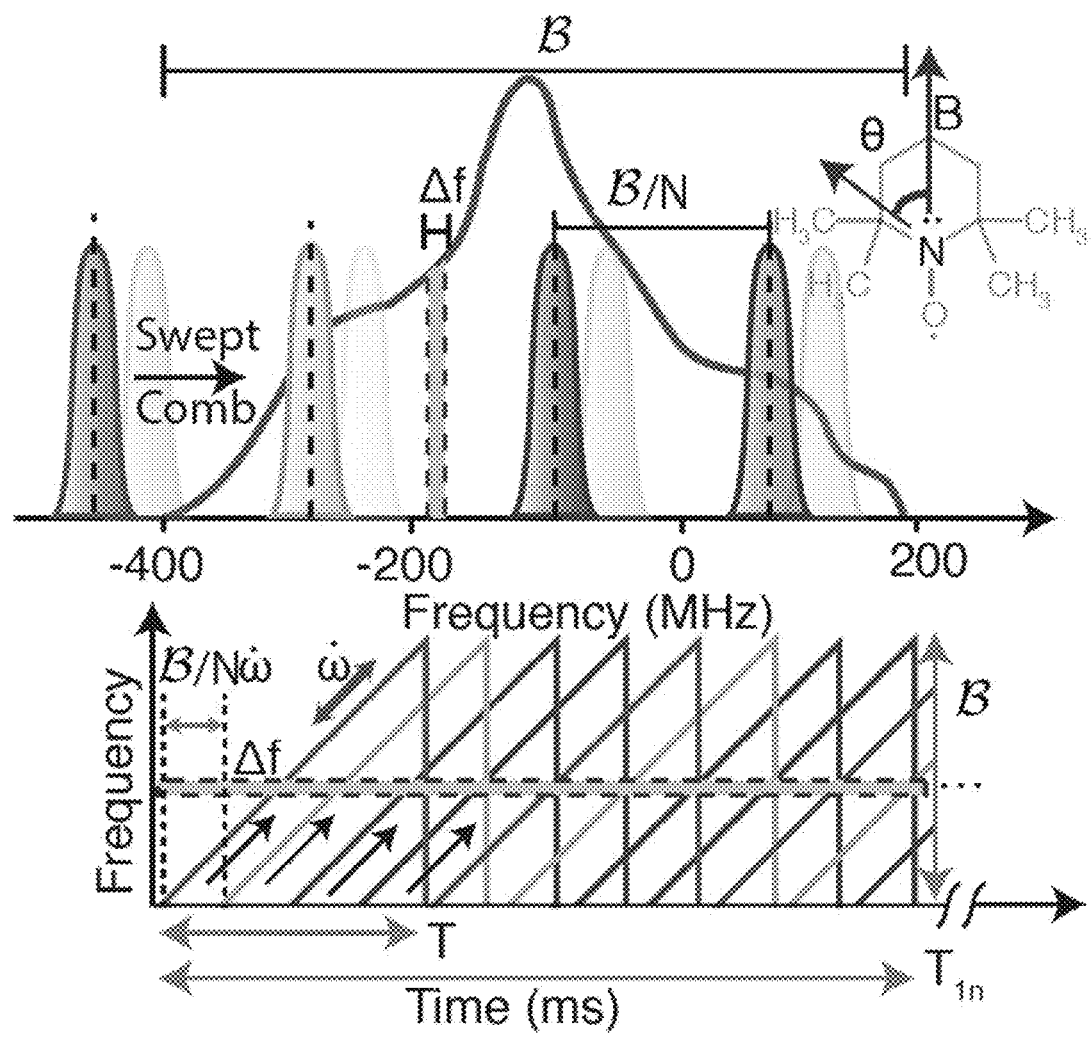
FIG. 24 illustrates a representation of a microwave frequency comb.
Figure 25:
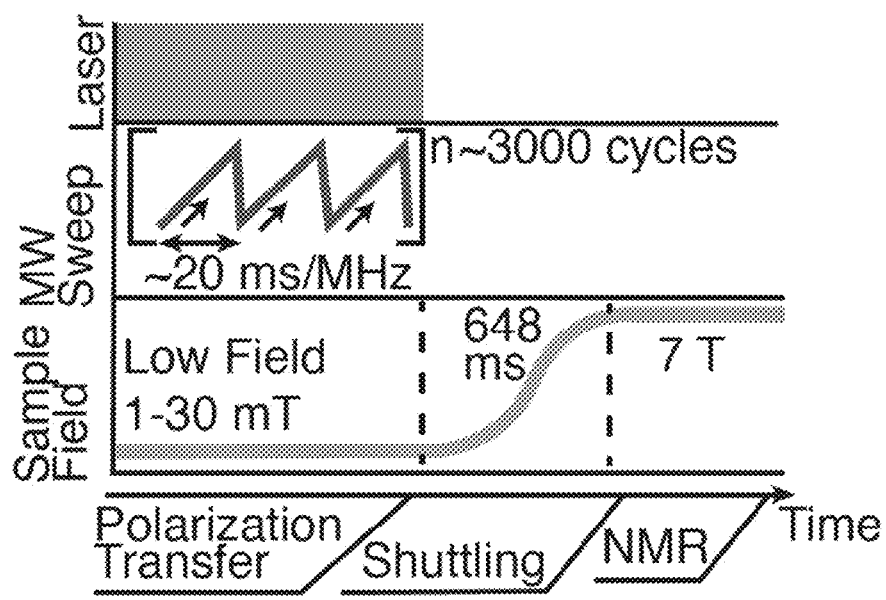
FIG. 25 illustrates a pulse sequence for hyperpolarization in diamond powder.

The embodiments here employ a simple method to overcome this bottleneck, increasing the effective number of polarization transfer events while maintaining the same optimal sweep adiabatic rates set by Landau-Zener conditions. The embodiments involve a swept microwave frequency-comb, that coherently and simultaneously sweeps the entire electron linewidth $\beta$ at d, while maintaining adiabaticity for each sweep over an individual electron packet as illustrated by FIG. 24. This allows repeated polarization transfer from each successive sweep of the comb, allowing one to gain a multiplicative DNP enhancement boost. Intuitively, the individual comb teeth can be as close as the homogenous electron linewidth $\Delta f\ 1/T_{2e}$ in frequency, and can sweep each electron packet as often as $t_{repol}$, allowing an enhancement gain $\varepsilon \to N_\varepsilon$, where $N \approx \langle \Delta f/\dot\omega t_{repol}\rangle$. The potential gains in hyperpolarization enhancements, stemming from this multiplicative boost can be significant. For instance, for the case of TEMPO at 5 T considered above, with $\Delta f \approx 1$ MHz, one can obtain DNP boosts by over an order of magnitude. More importantly, since the microwave power for each sweep remains e, the technique can be relatively easily implemented with existing technology, the frequency comb being constructed by time-cascading sweeps from N separate low-power amplifiers.

While the method is very general, for purposes of understanding the application to the hyperpolarization of $^{13}$C nuclei in microdiamond powder via optically polarized electron spins associated with Nitrogen Vacancy (NV) center defects intrinsic to the diamond.

There has been long standing interest in hyperpolarized micro- and nanodiamond particles, because their inherently high surface area provides an attractive means to hyperpolarize liquids brought in contact with them. The embodiments result from a recently developed a method for the room temperature optical DNP of $^{13}$C nuclei in powdered diamond, employing a combination of laser and swept microwave irradiation at low magnetic fields (B ~1-30 mT). The method, while sharing implementational similarities with ISE differs in that it is a predominantly low-field mechanism, polarizing spins for which $\omega_L \ll A$; and where the hyperpolarization sign is under complete experimental control. The spin-1 NV centers are inhomogenously broadened to a powder pattern with bandwidth $\beta = \gamma_e B$, and here too the slow rate of microwave sweeps over B limit the overall achievable nuclear polarization. This is particularly pertinent since the NV electrons can be completely and rapidly repolarized by laser irradiation with $t_{repol} \ll T1e$, scaling with the applied laser power. As the embodiments shall show swept frequency combs allow for multifold DNP gain with little hardware overhead.

Figure 26:
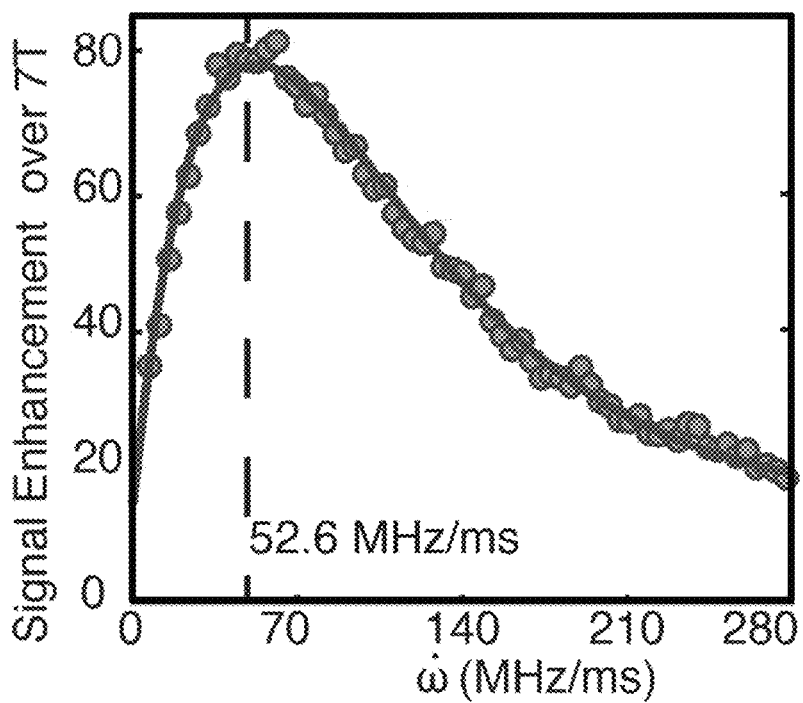
FIG. 26 illustrates an embodiment of a sweep rate for hyperpolarization in diamond powder.
Figure 27:
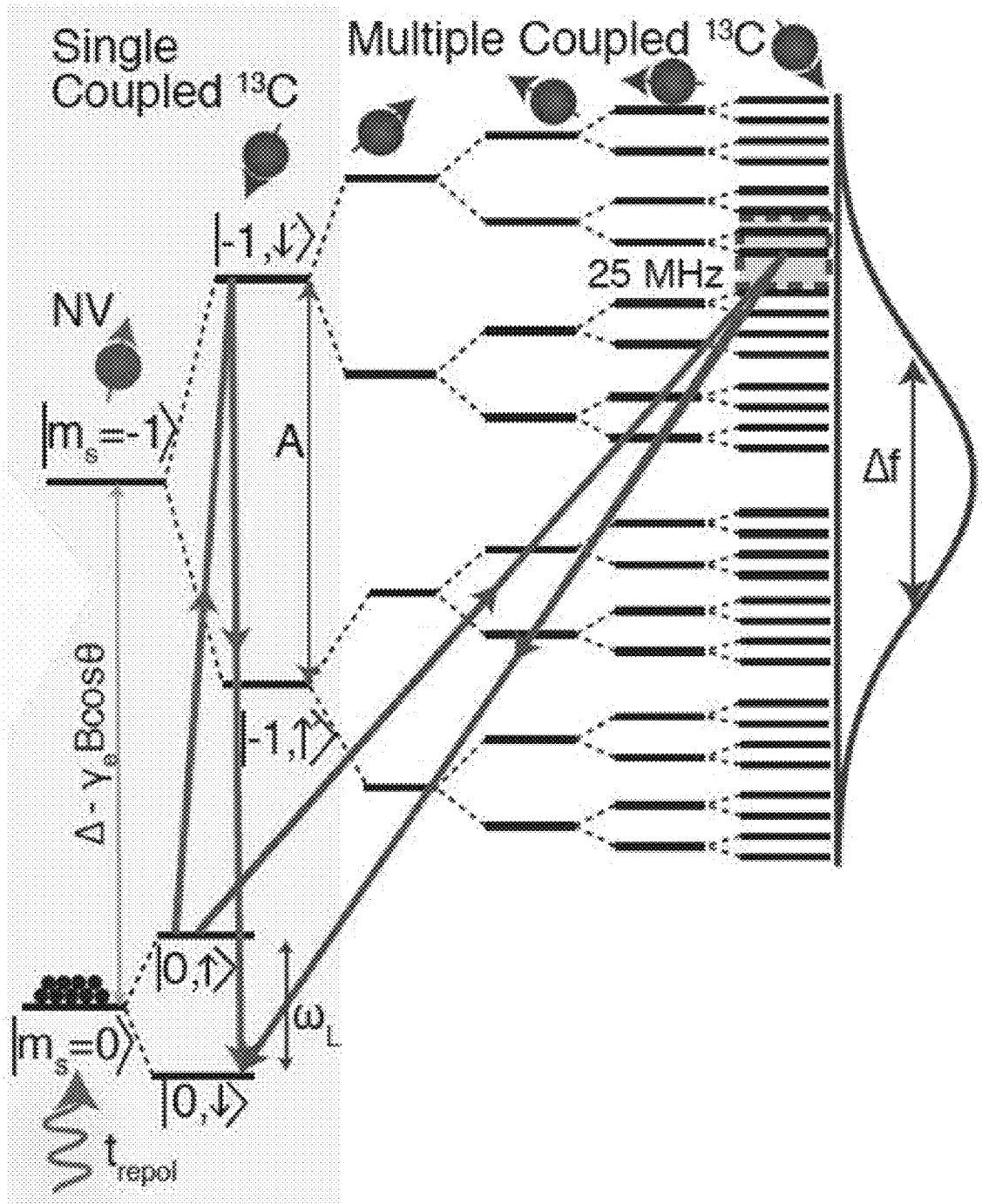
FIG. 27 illustrates a graphical representation of a DNP mechanism in diamond powder.
Figure 28:
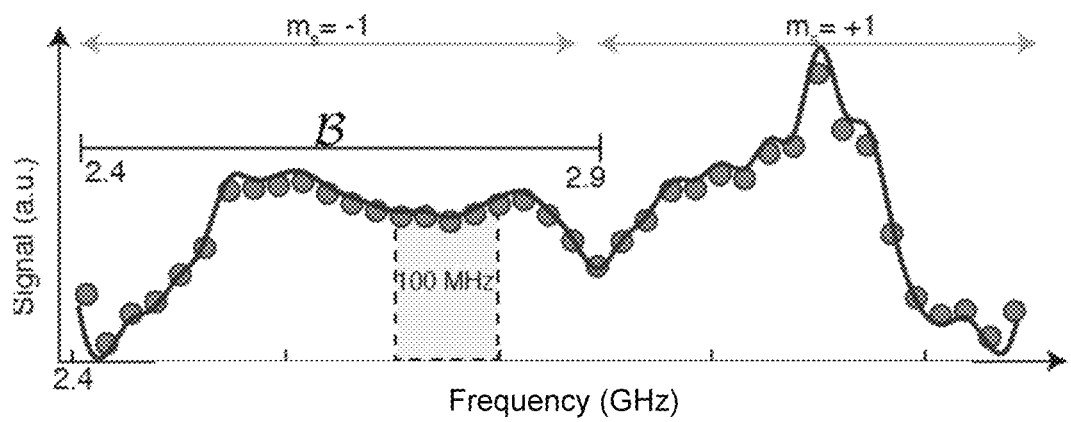
FIG. 28 illustrates an indirect mapping of ESR lineshape.
Figure 34:
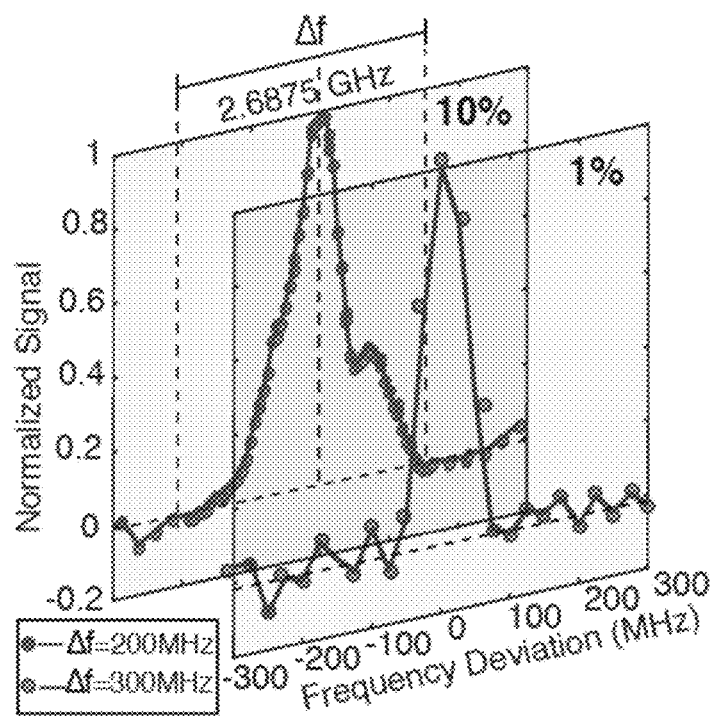
FIG. 34 illustrates indirectly mapped ESR spectra.

To assist in understanding, a first embodiment illustrates the DNP mechanism for the case of an NV center coupled to a single $^{13}$C nuclear spin shown in FIG. 28. Laser irradiation polarizes the NV centers to the $m_s=0$ state, and swept microwaves with Rabi frequency $\Omega \ll \omega_L$ implement a sequence two transition-selective rapid adiabatic passages (RAPs) in quick succession, transferring population to the nuclear spin via levels in the $m_s=\_1$ manifolds (for clarity only the $m_s=\pm 1$ manifold is depicted in FIG. 27). Given a typical sweep rate of $\dot{\omega}$=52 MHz/$m_s$ shown in FIG. 26, each of the individual transitions are traversed in $\omega_L/\dot{\omega}$=4.5 µs, and to a good approximation at the excitation powers employed, the laser does not significantly repolarize the NV during this traversal period. There is consequently a coherent transfer of polarization via the swept microwaves, enabling $^{13}$C DNP the sign of which only depends on the exact order in which the transitions are excited, or equivalently to the direction of the microwave sweep. Indeed, the $^{13}$C nuclei are hyperpolarized aligned (anti-aligned) to B under microwave sweeps from low-to-high (high-to-low) frequencies. The optimal sweep rate $\dot{\omega}$ is set by a compromise between maintaining adiabaticity for individual sweeps, and increasing the overall number of sweeps in the total pumping period referring to FIG. 26. Since the $m_s=\pm 1$ manifold states just act as intermediaries for population transfer, the DNP mechanism is independent of NV center orientation, hence enables the hyperpolarization of diamond powders. When considering the more realistic scenario of multiple $^{13}$C nuclei coupled to the NV center, one obtains in general a continuum of levels stemming from the hierarchy of the hyperfine interactions, the density of states reflecting the underlying homogeneous electron linewidth as shown in FIG. 34. This broadening is in general proportional to the relative concentration of electrons (radicals) employed for DNP. For NV centers, there is additional broadening due to interaction with nitrogen defects (P1 centers) in the diamond. Sweeping of over any small spectral window in FIG. 27 leads to hyperpolarization, the sign of which still depends on the direction of sweep as shown in FIG. 28.

However, the electron resonance frequencies $\Delta\pm\gamma_e B \cos\vartheta$ are orientation dependent, where $\Delta$=2.87 GHz and $\vartheta$ is the angle from the applied field to the N-V axis. In a randomly oriented powder the ESR spectrum is hence inhomogenously broadened to B=$\gamma_e$B$\approx$600 MHz at 20 mT. Indeed in FIG. 28 it indirectly maps this spectrum from the $^{13}$C enhancement, by performing DNP over small (100 MHz) windows swept over in frequency space. These experimental results are for the case of 200 m diamond microparticles (Element6) containing a natural abundance (1.1%)$^{13}$C and $\approx$1 ppm of NV centers. Since the mechanism of the embodiments relies on maintaining transition selectivity for the RAPs, the Rabi frequency must maintain $\Omega_e$=<$\omega_L$=200 kHz, and limits the maximum employ able sweep rate ca. Consequently, the large B leads to a long MW sweep time T=$\beta/\dot{\omega}\approx$12 $m_s$ that far exceeds the repolarization time, T>T$_{1e}$>t$_{repol}$ and bottlenecks the DNP enhancement.

Frequency combs provide an elegant means to overcome this problem, decoupling the MW sweep rate from the total number of electron sweeps. Indeed, a swept microwave frequency comb can maintain the adiabaticity of a single sweep while increasing the cumulative number of sweeps in the total DNP period bounded by nuclear relaxation time T1n. Microwave frequency combs can be constructed by semiconductor lasers under negative optoelectronic feedback and nonlinear mixing in tunneling junctions. The embodiments here follow a simpler approach instead, time-cascading MW sweeps generated by N voltage controlled oscillator (VCO) sources.

Figure 29:
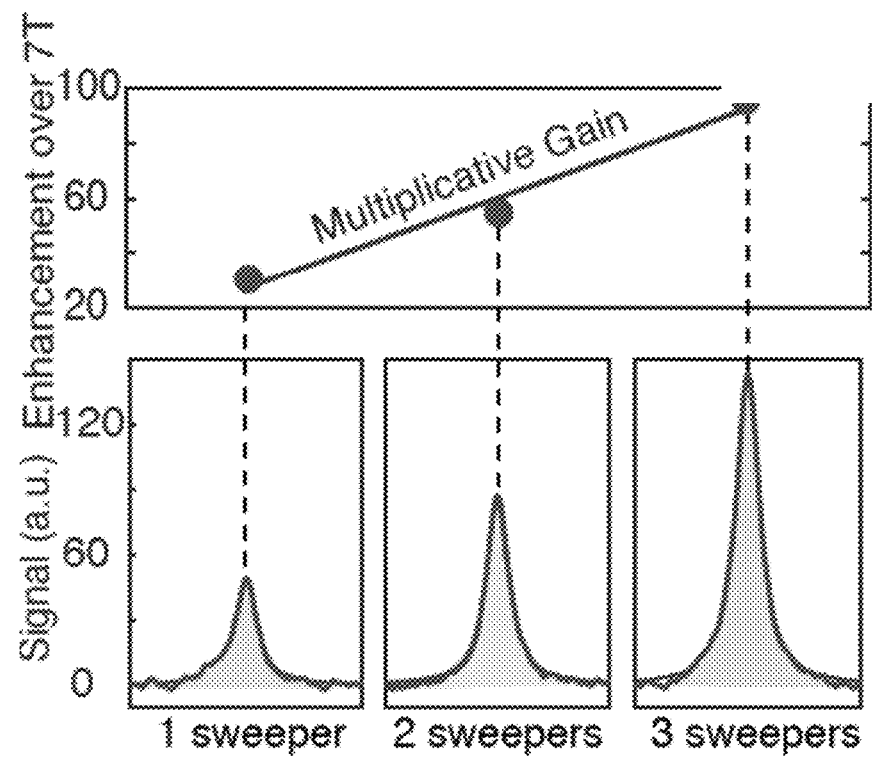
FIG. 29 illustrates a graph of enhance DNP gains using frequency combs.

The DNP enhancement gains scale linearly with N, allowing a multiplicative boost to the DNP enhancement as in FIG. 29 from 30× to 100× over 7 T. Note that all the sources sweep the entire bandwidth β, and the frequency ramps are time-shifted by $\beta$=/(N $\dot{\omega}$) to maximize the period between successive sweeps as in FIG. 13. While one could consider an alternate scenario where B is partitioned into N sub-bands which are swept by individual sources, the current strategy performs better since the electrons at the boundaries between the frequency partitions are also swept across completely, as required for optimal LZ population transfer. The individual VCOs have slightly different frequency-voltage characteristics, and to cascade them effectively the process matches their exact sweep bandwidths to within $\Delta$f<1 MHz via a fast-feedback algorithm. The sources are then power combined and amplified, and to prevent intermodulation distortion (IMD) artifacts the process ensures that the amplifier is operated far below compression.

It is worth mentioning that in effect, the cascaded sweeps entail an increase of total microwave power seen by the sample. For DNP mechanisms such as ISE, the same gains in principle can be achieved by employing a higher MW power, leading to a faster $\Omega_e$ and consequently ca. However even for such systems, there are several technological advantages of using swept frequency combs for DNP. The costs of MW sources and amplifiers scale approximately exponentially with power, but employing a cascade of N low-power amplifiers leads to only a linear cost scaling. Moreover, it is easier to directly synthesize slower frequency sweeps, for instance using inexpensive AWGs and mixers. The embodiments here allow one to harness several slow, low-power, sweeps to gain the advantages of more expensive high-power platforms, an advantage especially pertinent at high fields. Moreover, the technique highlights the inherent merits of frequency swept modalities as opposed to field swept ones; while they are equivalent for a single sweep, when cascaded into swept frequency combs the former can provide multifold DNP gains.

Figure 30:
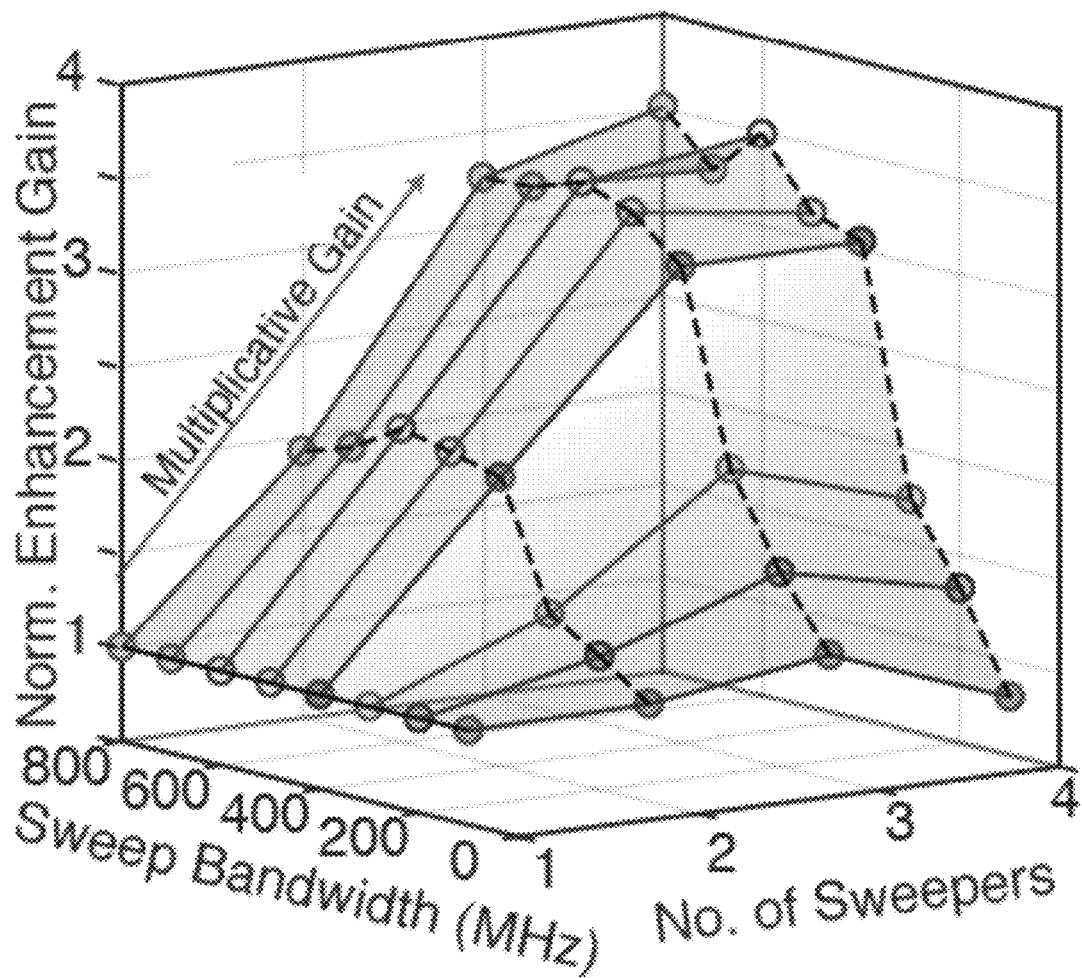
FIG. 30 illustrates a graphical representation of bandwidth dependence.
Figure 33:
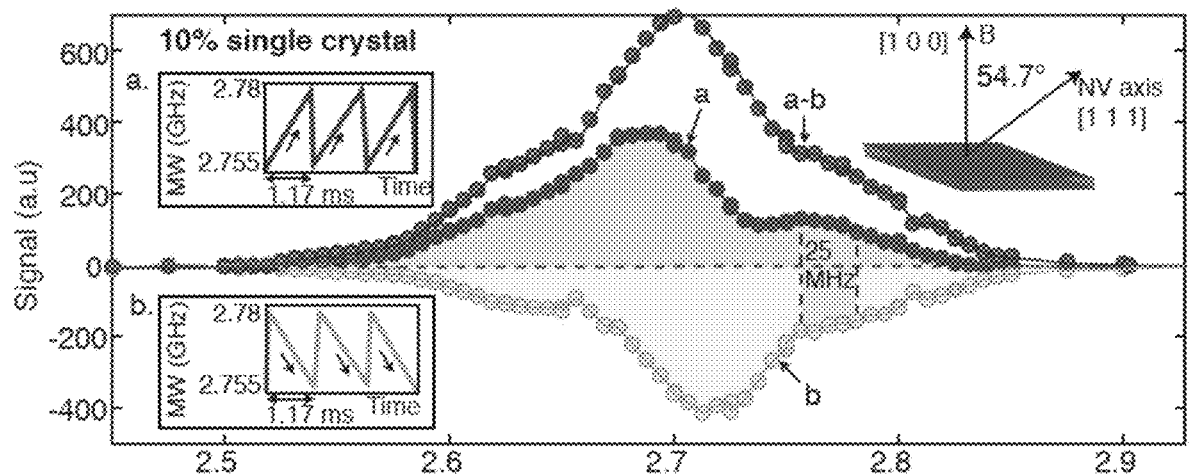
FIG. 33 illustrates an ESR lineshape of a sample mapped indirectly via DNP.
Figure 35:
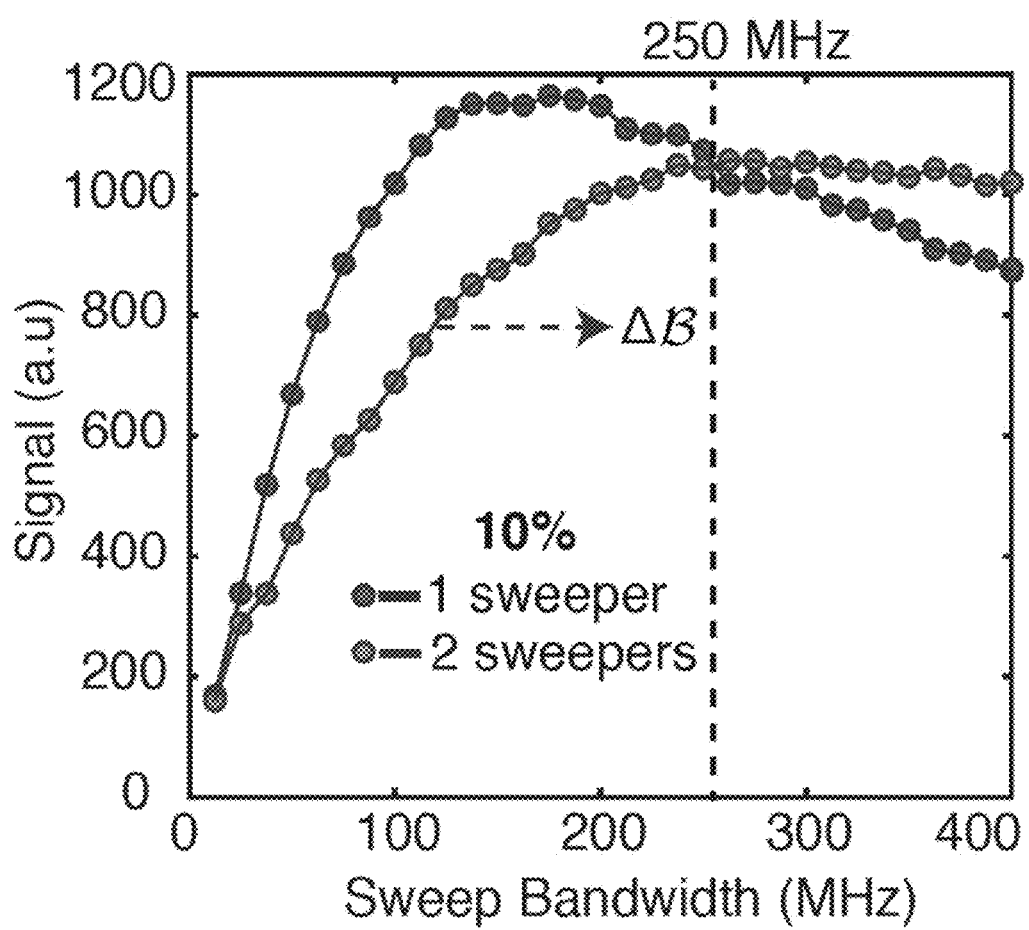
FIG. 35 illustrates results of 2 cascaded sweepers over a homogeneously broadened line.

The discussion now turns to evaluating the factors affecting the ultimate limits to the multiplicative enhancement gain. In FIG. 30, for a fixed (i, the process varies the sweep bandwidth, equivalent to bringing the frequency comb sweeps closer in frequency and time. One can observe that when the frequency comb teeth are separated by under $\approx$200 MHz, there is first a saturation in the DNP boosts and subsequent drop. This may be ascribed to the inherent limit set by homogeneous electron broadening $\Delta$f in the powder pattern, which can also be seen in FIGS. 33-35. When two sweeps occur simultaneously on different parts of the electron homogeneous line corresponding to a single NV center shown in FIG. 27, there is interference between them and consequently lower DNP enhancements. Note that in these experiments, the sweep times always exceeded trepol=100 µs, and limits set by $\Delta$f are the dominant ones.

Figure 31:
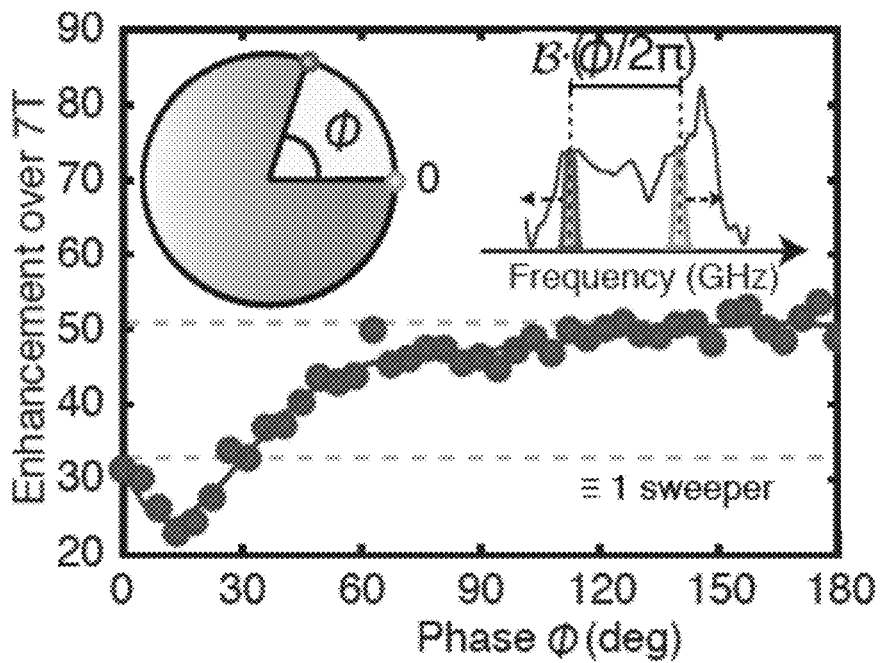
FIG. 31 illustrates a graph of data resulting from determining the optimal frequency for 2 sweeper combs.
Figure 32:
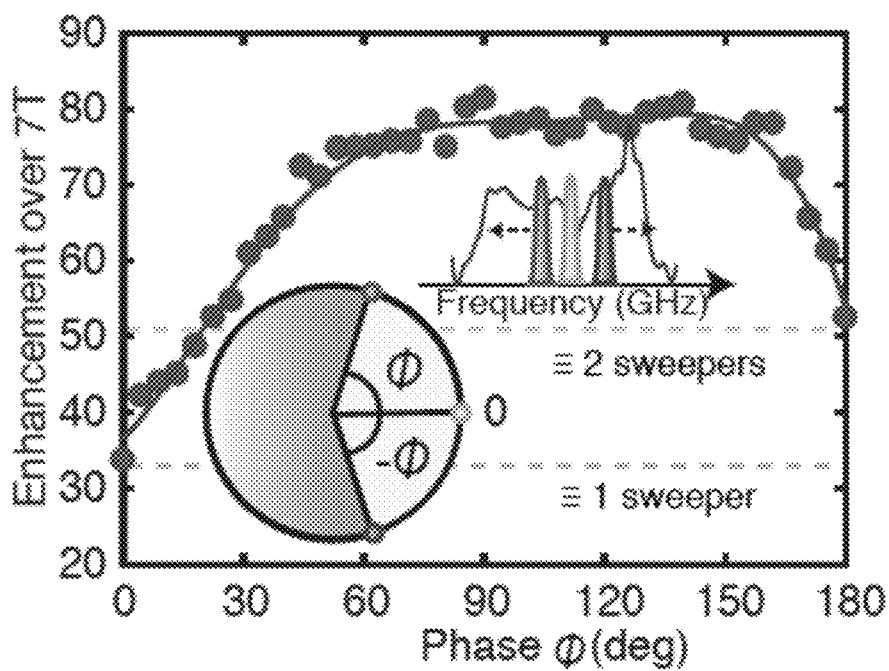
FIG. 32 illustrates a graph of data resulting from determining the optimal frequency for 3 sweeper combs.

This is also elucidated in FIGS. 31 and 32 studying the effects of bringing the frequency comb teeth closer together over a fixed bandwidth, by changing the phase Y between the time-cascaded ramps in FIG. 24. It is evident then how the enhancement gains arise: when all ramps have the same phase, the enhancement from the comb is identical to that employing a single sweeper, the dashed line in FIGS. 31 and 32, increasing as the ramps are phase-shifted, with the expected optimal DNP gains at phase separation $\varphi_{opt}$=2λ/N when the comb teeth are maximally separated in frequency and time. More importantly, the plateaus in FIGS. 31 and 32 indicate that the enhancement gains if the comb teeth are separated beyond $\Delta$f. To make this more concrete, in FIGS. 33-35, the homogeneous linewidths are studied by indirectly mapping the electron spectrum via $^{13}$C DNP, employing single crystals for these experiments and orienting the N-V axes at the magic angle such that there is no inhomogenous broadening. The results in FIG. 34 demonstrate the growing $\Delta f$ with increasing $^{13}C$ enrichment, arising from hyperfine couplings of FIG. 27. As is to be expected, there are no DNP enhancement gains to be obtained by employing a swept frequency comb when the comb frequencies are closer than $\Delta f$, shown in FIG. 35. Overall, FIGS. 31-35 demonstrate the inherent constraints of the technique, and in the ultimate limit, the frequency combs approach an excitation of all $\Delta f$-wide electron packets at once, sweeping them as often as $t_{repol}$, equivalent to a pulsed DNP experiment over the entire electron bandwidth.

Figure 36:
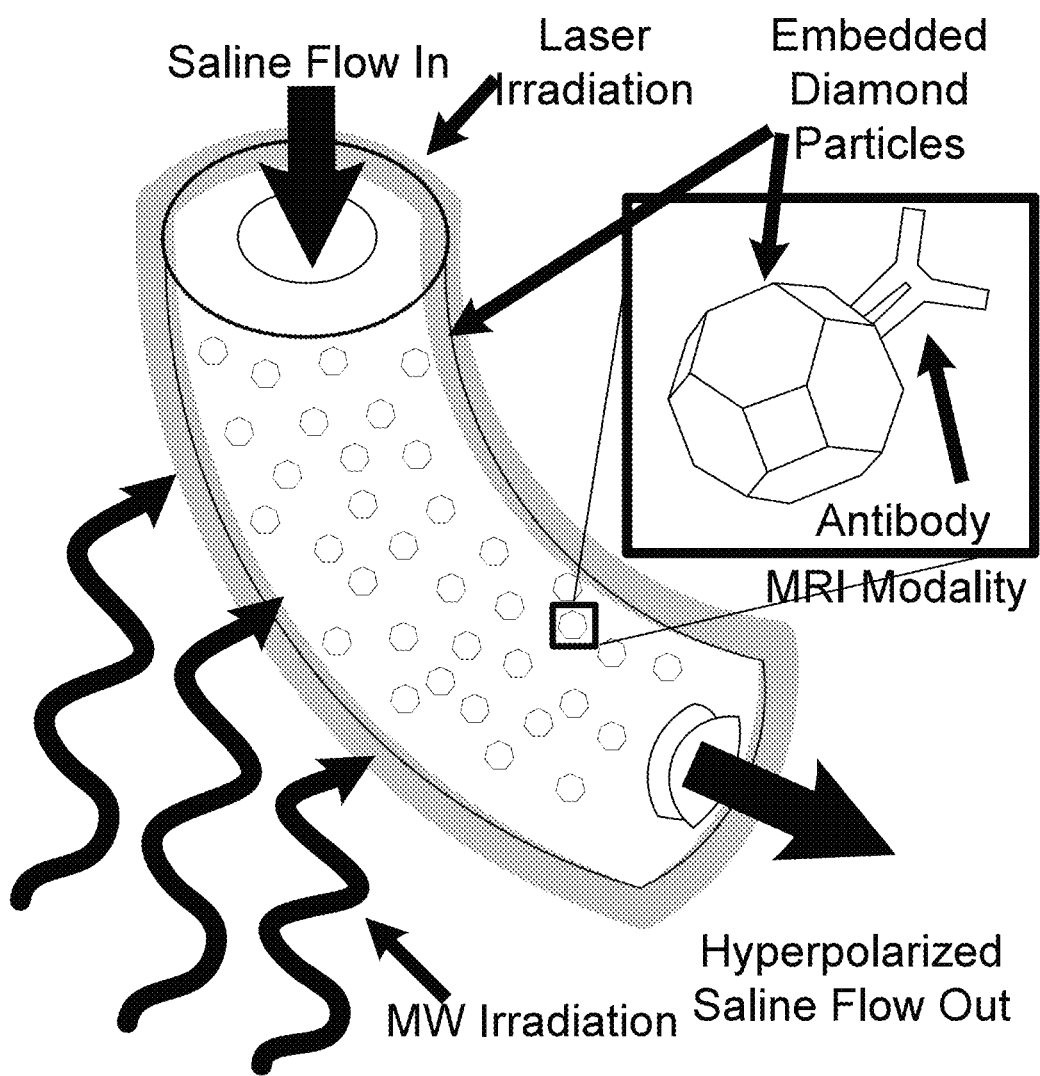
FIG. 36 illustrates a diamond-dressed narrow-channel hyperpolarizer used to transfer hyperpolarization to liquids via flow.

The embodiments allow the transfer of hyperpolarization to liquids via flow through $^{13}C$ polarized diamond frit for signal enhanced spectroscopy or imaging as in FIG. 36 Particularly compelling is the generation of hyperpolarized saline for signal enhanced MR angiography. Alternatively the hyperpolarized, surface functionalized, particles could be used as MRI tracers for tumor detection.

Figure 37:
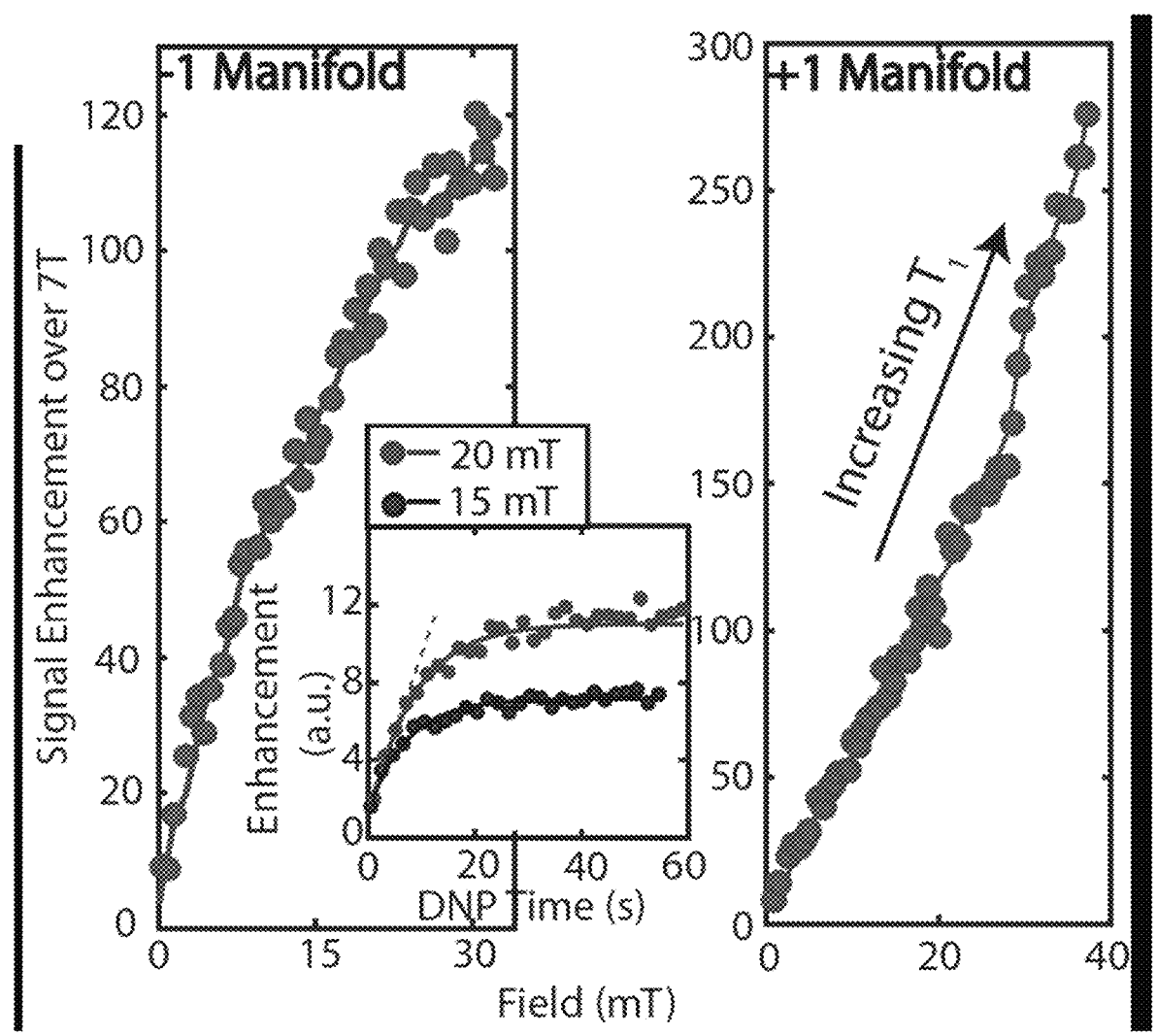
FIG. 37 illustrates a graph of field dependence measurements of DNP enhancement in the range of 1-38 mT.

In FIG. 37 we determine the field dependence of DNP enhancements under 40 s of optical pumping for sweeps over either NV manifold. MW sweep rate conditions were kept optimal for each field value (described below). Data indicates that the DNP enhancements increase sharply with field, with the $m_s=-1$ manifold appearing to saturate beyond $\approx 35$ mT. This dependence arises from the inter-play of two factors with increasing $B_{pol}$: (i) a dominant rise in 13C nuclear $T_1$ lifetimes and (ii) a fall in the integrated electron transition probability $\int \pi/2\ 0\ P(\vartheta)d\vartheta$.

Figure 38:
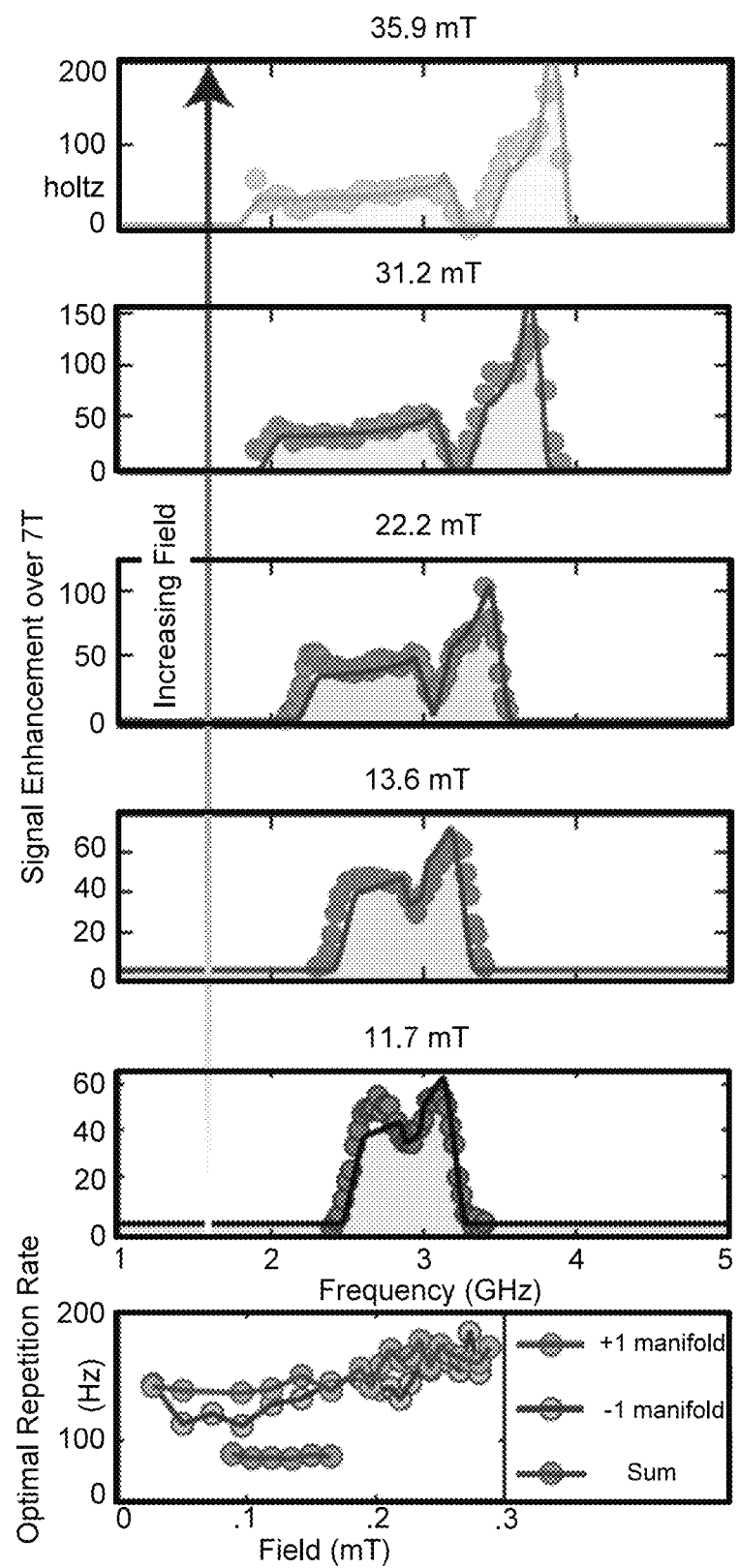
FIG. 38 illustrates NV center ESR spectra mapped directly by hyperpolarized $^{13}C$ NMR at various fields.

For various $B_{pol}$ fields, we map in FIG. 38 the NV ESR spectra via the $^{13}C$ enhancements in a 100 MHz window, with good agreement with the corresponding calculated spectra (solid lines). As expected the spectra become wider at higher fields. The enhancements per 100 MHz window obtained in the $m_s=-1$ manifold is smaller than the $m_s=+1$ manifold since (inset of FIG. 38) there is a relative reduction of electron density of states per unit frequency bandwidth. At 36 mT, for instance, a single 100 MHz sweep window in the $m_s=+1$ manifold can provide DNP enhancements approaching 200 over 7 T. Indeed the frequency spread in the $m_s=-1$ manifold grows approximately linearly with field, while in the $m_s=+1$ manifold it saturates after an initial quadratic rise. Experiments indicate therefore that $^{13}C$ hyperpolarization follows the native NV electron density of states, reflecting that it is the weakly coupled $^{13}C$ nuclei that are predominantly polarized.

Figure 39:
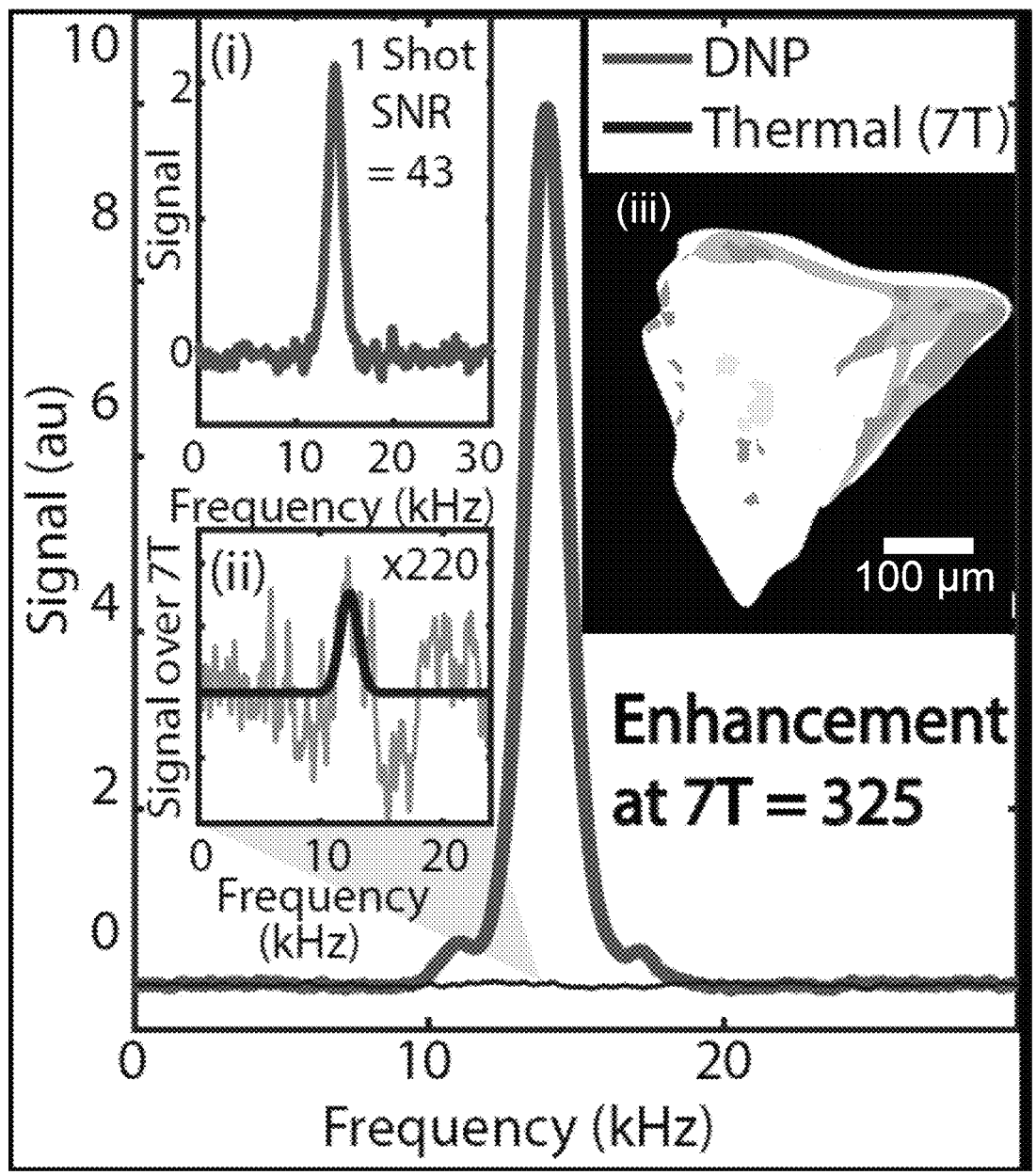
FIG. 39 illustrates single particle DNP enhancement that is $^{13}C$ enhanced.

FIG. 39 shows the hyperpolarized spectrum from a single 400 μm particle that is 10% enriched $^{13}C$. The bulk polarization after 60 s of optical DNP exceeded >0.32% (enhanced over 7 T by $\varepsilon=325$), allowing the detection of the single particle with a single shot SNR$\approx 43$, a speed-up in measurement time compared to that at 7 T by $\varepsilon^2\ T_1(7T) \approx 10^6$. The $T_{1\ (B_{pol})}$ ability to efficiently detect single particles, coupled with their low toxicity, allows MRI modalities constructed out of surface functionalized diamond particles.

Figure 40:
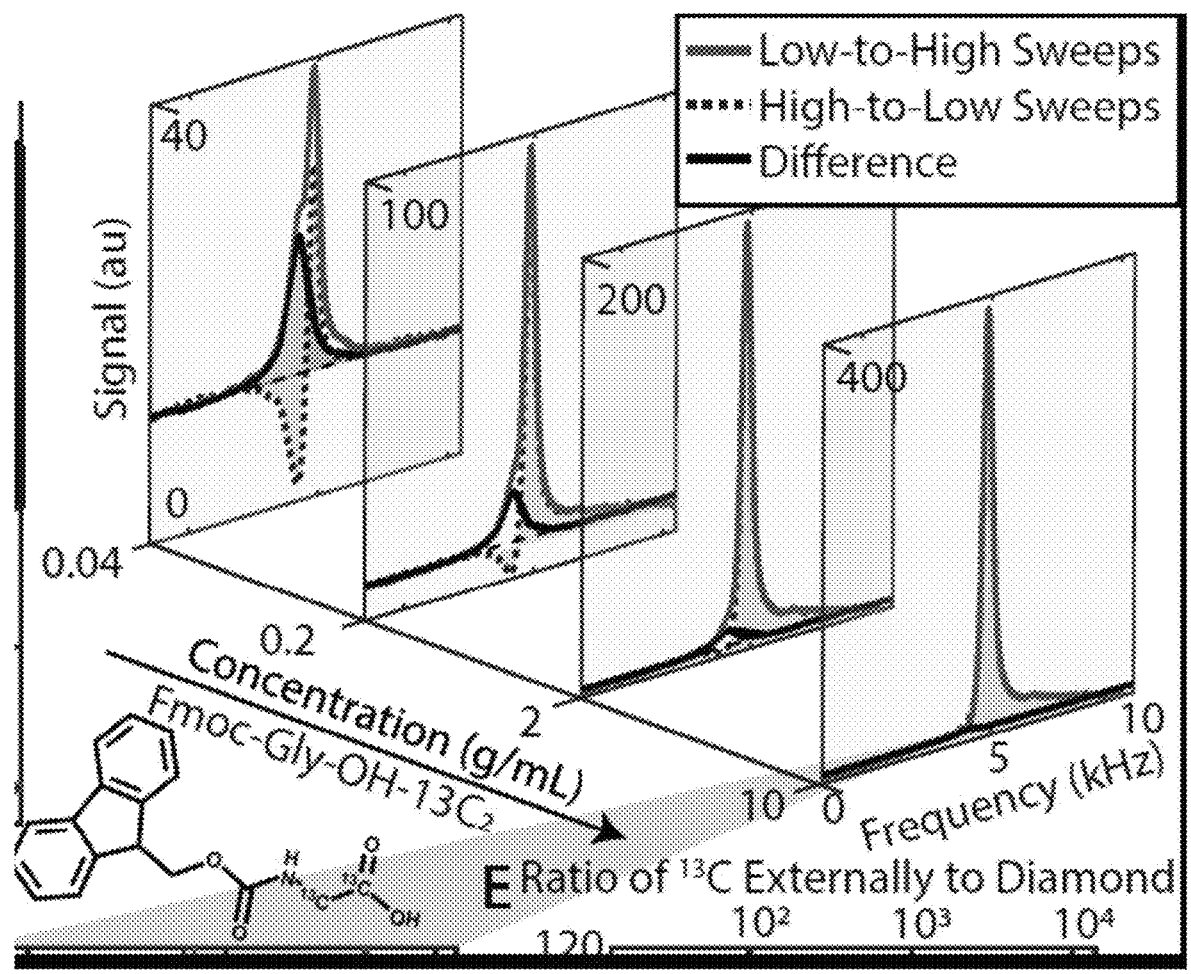
FIG. 40 illustrates background suppression by exploiting successive sign-reversals of $^{13}C$ hyperpolarization.
Figure 41:
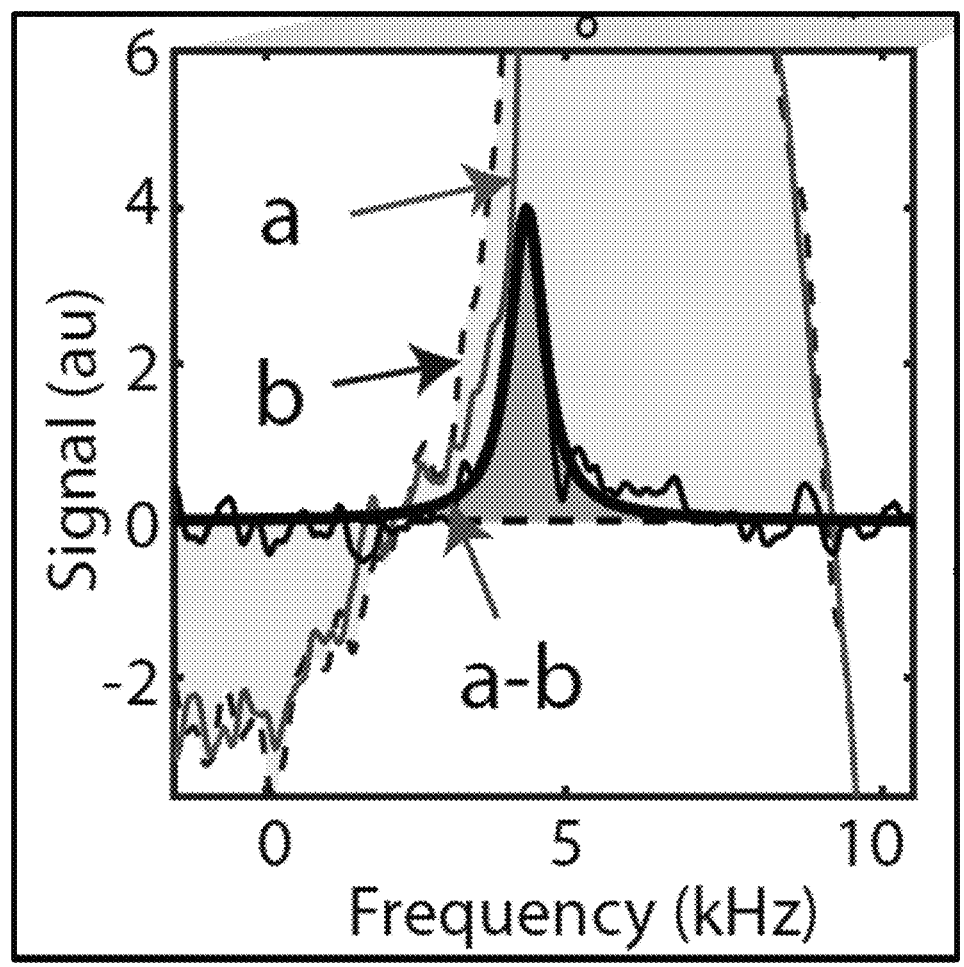
FIG. 41 illustrates a zoomed signal employing background suppression.

Since the signal from the $^{13}C$ in the diamond can be sign inverted with high fidelity, (better than 5%, see FIG. 40), the MRI signals can be background suppressed—allowing robust recovery of the $^{13}C$ signal from the hyperpolarized particles although buried in a large external $^{13}C$ background. FIG. 5C shows DNP performed on natural abundance 200 μm diamond particles embedded in an increasing concentration of Fmoc-Gly-OH-$^{13}C_2$, a $^{13}C$-enriched biological compound with a chemical shift (−53.6 ppm) which closely overlaps the diamond peak (−61 ppm). By performing successive experiments with alternate MW sweep direction and subtracting the result, we are able to suppress the compound peak and exclusively recover the diamond signal although it is initially impossible to discern (see FIG. 41). The signal suppression, (a−b)/a, we achieve exceeds two-orders of magnitude corresponding to a $^{13}C$ suppression ratio exceeding $10^4$ (upper axis). This remarkably high value is a consequence both of hyperpolarization as well as controllable sign reversals.

FIG. 42 shows an embodiment consisting of a setup detailing a multiple fiber coupled laser configuration. By employing multiple low-powered lasers coupled with fiber optics, one can easily create various modalities to optically irradiate samples of large areas or for uniform distributions.

The method entails a swept frequency comb to excite the entire inhomogenously broadened electron bandwidth for polarization transfer. It can be implemented by cascading N sweeps from individual low-power sources/amplifiers to obtain a DNP enhancement boost a N, with ultimate limits set by the homogeneous electron linewidth and lifetime $T_{1e}$. As such the technique affirms the notion the electron spin control can significantly enhance DNP by harnessing the full power of the electron spectrum. The embodiments have demonstrated its utility for the hyperpolarization of $^{13}C$ nuclei in powdered diamond microparticles via optically pumped NV centers at room temperature, obtaining a 300% boost in DNP efficiency. When employed for conventional polarizing radicals at high fields, the technique promises to yield DNP enhancement boosts in excess of one order of magnitude, with relatively a simple implementation employing existing technology and only a.

Figure 43:
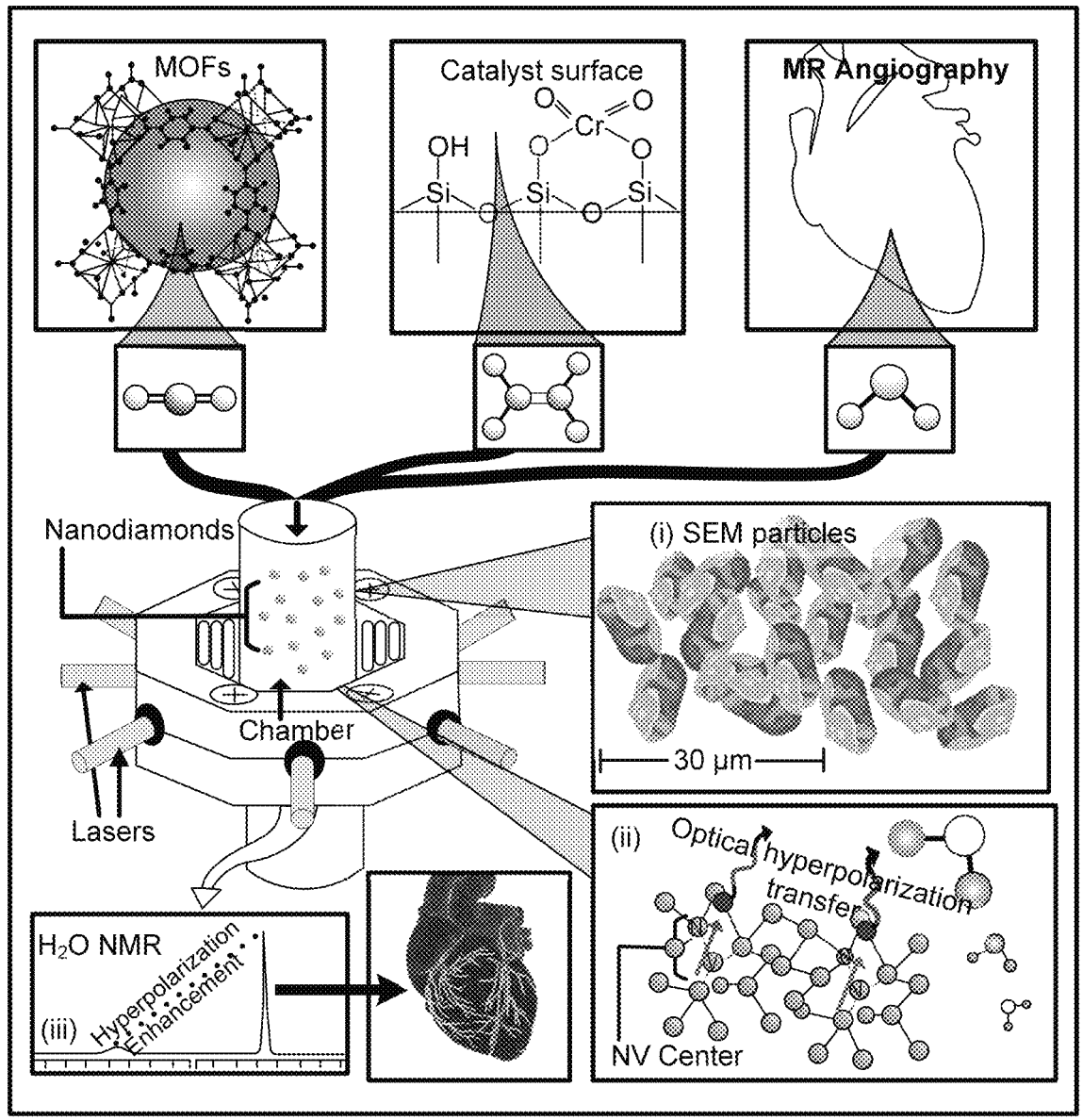
FIG. 43 illustrates potential applications of the diamond hyperpolarization device.

FIG. 43 shows potential applications of the diamond hyperpolarization device. Replenishable optical hyperpolarization to illuminate materials and reactions. The use of optical and microwave excitation hyperpolarizes diamond particles in a chamber. (i) Typical particle SEM. (ii) Hyperpolarization can be coaxed into liquid in contact with the high surface area particles. Hyperpolarization in benign fluids like water, CO2 open several applications for "lighting-up" structure and dynamics in (A) Nanoporous materials and MOFs, (B) Catalyst surfaces, (C) and in biomedical applications such as MR angiography. (D) Hyperpolarized water illuminates the heart arteries and may provide a rapid, non-toxic means for disease diagnosis.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:
1. A system, comprising:
   a superconducting or permanent magnet;
   a high field portion corresponding to the superconducting or permanent magnet, wherein the high field has a range of 0.1-20 T;
   a low field portion positioned adjacent a magnetic shield, the magnetic shield between the low field portion and the superconducting or permanent magnet, wherein the low field has a range of 0.01 nT-100 mT;
   a shuttling mechanism connected to the high field portion and the low field portion configured to transport a sample between the low field portion and the high field portion; and
   a polarization sub-assembly comprising a microwave source configured to apply microwaves to the sample and a laser configured to continuously apply laser light to the sample simultaneous to the microwaves to hyperpolarize the sample while the sample is within the low field portion.

2. The system of claim 1, wherein the shuttling mechanism includes a servo motor.

3. The system of claim 1, wherein the shuttling mechanism includes a pneumatic motion device.

4. The system of claim 1, wherein the substance includes diamond particles in single-crystal, or micro-sized or nano-sized powder.

5. The system of claim 1, wherein the shuttling mechanism includes:
a conveyer belt;
a rod; and
a tube attached to the rod and configured to travel along the conveyer belt.

6. The system of claim 5, wherein the rod is made of carbon fiber.

7. The system of claim 1, wherein the shuttling mechanism has a shuttling speed up to 2 m/s with an acceleration of up to 30 m/s$^2$.

8. The system of claim 1, wherein the superconducting magnet is a nuclear magnetic resonance (NMR) magnet.

9. A method of hyperpolarizing substances, comprising:
applying optical illumination to a substance;
irradiating the substance with a series of microwave signals as one of either a single signal or as a frequency comb to hyperpolarize the nuclei in the substance; and
coaxing hyperpolarization into nuclear spins of one of a surrounding solid or fluid.

10. The method of claim 9, wherein the substance includes diamond particles in single-crystal, or micro-sized or nano-sized powder.

11. The method of claim 10, where the signal from the $^{13}$C in the diamond can be sign inverted with high fidelity.

12. The method of claim 11, wherein diamonds are used as agents to background suppress NMR/MRI signals.

13. A portable hyperpolarizer, comprising:
a sample holder configured to hold a sample;
a laser source configured to direct optical illumination at the sample in the sample holder;
at least one microwave generator to direct microwaves at the sample, such that the optical illumination and the microwaves cause hyperpolarization in the sample: and
a housing configured to support the sample holder, the laser diode, and at least one microwave generator.

14. The hyperpolarizer of claim 13, further comprising an interface to at least one of either a nuclear magnetic resonance spectrometer or a magnetic resonance imaging machine.

15. The hyperpolarizer of claim 13 configured to serve as a contrast agent for magnetic resonance imaging (MRI).

16. The hyperpolarizer of claim 13, wherein the housing is compact, rigid, and lightweight.

17. The hyperpolarizer of claim 16, wherein the housing is made of aluminum.

18. The hyperpolarizer of claim 13, wherein the laser source includes a laser diode.

19. The hyper polarizer of claim 13, wherein the laser source includes a multiple fiber coupled laser configuration.

20. The hyperpolarizer of claim 13, wherein the substance includes diamond particles in single-crystal, or micro-sized or nano-sized powder.

21. The hyperpolarizer of claim 13, wherein the hyperpolarization in the sample is transferable to one of either an external solid or an external liquid.

22. The hyperpolarizer of claim 13 configured with tubing for liquid flow of polarized diamond samples and surrounding liquid to and from the device.

* * * * *